United States Patent
Clarysse et al.

(10) Patent No.: US 7,751,035 B2
(45) Date of Patent: Jul. 6, 2010

(54) METHOD AND DEVICE TO QUANTIFY ACTIVE CARRIER PROFILES IN ULTRA-SHALLOW SEMICONDUCTOR STRUCTURES

(75) Inventors: Trudo Clarysse, Antwerpen (BE); Janusz Bogdanowicz, Liège (BE)

(73) Assignees: IMEC, Leuven (BE); Katholieke Universiteit Leuven, Leuven (BE)

(*) Notice: Subject to any disclaimer, the term of this patent is extended or adjusted under 35 U.S.C. 154(b) by 181 days.

(21) Appl. No.: 12/043,906

(22) Filed: Mar. 6, 2008

(65) Prior Publication Data

US 2008/0224036 A1 Sep. 18, 2008

Related U.S. Application Data

(63) Continuation of application No. PCT/EP2006/008709, filed on Sep. 7, 2006.

(30) Foreign Application Priority Data

Sep. 7, 2005 (GB) .................................. 0518200

(51) Int. Cl.
*G01N 23/00* (2006.01)
*G01N 21/00* (2006.01)
*G01B 15/00* (2006.01)
*H01L 21/00* (2006.01)

(52) U.S. Cl. .................... 356/237.1; 356/432; 356/445; 324/752; 324/750; 438/7; 250/307; 250/310; 702/155

(58) Field of Classification Search ............. 356/237.1, 356/432, 445; 324/752, 750; 438/7; 250/307; 250/310; 702/155

See application file for complete search history.

(56) References Cited

U.S. PATENT DOCUMENTS

| 6,049,220 A | 4/2000 | Borden et al. |
| 6,323,951 B1 * | 11/2001 | Borden et al. ............... 356/502 |
| 7,133,128 B2 * | 11/2006 | Clarysse et al. .......... 356/237.2 |

(Continued)

FOREIGN PATENT DOCUMENTS

WO WO 99/64880 A 12/1999

OTHER PUBLICATIONS

Zhou, et al., Use of a new thermal wave technology for ultra-shallow junction implant monitoring, Ion Implantation Technology Proceedings, 1998 International Conference in Kyoto, Japan, IEEE, vol. 1, Jun. 22, 1998.

(Continued)

*Primary Examiner*—Nikita Wells
(74) *Attorney, Agent, or Firm*—Knobbe Martens Olson & Bear LLP

(57) ABSTRACT

A method and device for determining, in a non-destructive way, at least the active carrier profile from an unknown semiconductor substrate are disclosed. In one aspect, the method comprises generating 2 m independent measurement values from the m reflected signals and correlating these 2 m measurement values with 2 m independent carrier profile values. The method further comprises generating additional 2 m measurement values to allow determining the active carrier profile and a second parameter profile by correlating the 4 m measurement values with the 4 m profile values. The method further comprises generating a total of 2 m[n.k] measurement values to allow determining [n.k] independent material parameter depth profiles, each material parameter profile having m points.

24 Claims, 17 Drawing Sheets

U.S. PATENT DOCUMENTS

| | | |
|---|---|---|
| 2003/0043382 A1 | 3/2003 | Borden et al. |
| 2004/0196464 A1 | 10/2004 | Akutsu et al. |
| 2004/0253751 A1 | 12/2004 | Salnik et al. |
| 2007/0292976 A1* | 12/2007 | Clarysse et al. ............... 438/7 |

OTHER PUBLICATIONS

Nicolaides, et al., Non-destructive analysis of ultra shallow junctions using thermal wave technology, Review of Scientific Instruments, vol. 74, No. 1, Jan. 2003.

Dortu, et al., Progress in the physical modeling of carrier illumination, Proceedings of Eighth International Workshop on Fabrication, Characterization, and Modeling of Ultra-Shallow Doping Profiles in Semiconductors, Jun. 5-8, 2005, Daytona Beach, Florida.

Clarysse, et al., Towards non-destructive carrier depth profiling, Proceedings of Eighth International Workshop on Fabrication, Characterization, and Modeling of Ultra-Shallow Doping Profiles in Semiconductors, Jun. 5-8, 2005, Daytona Beach, Florida.

International Search Report & Written Opinion dated Jan. 23, 2007 for PCT/EP2006/008709.

* cited by examiner

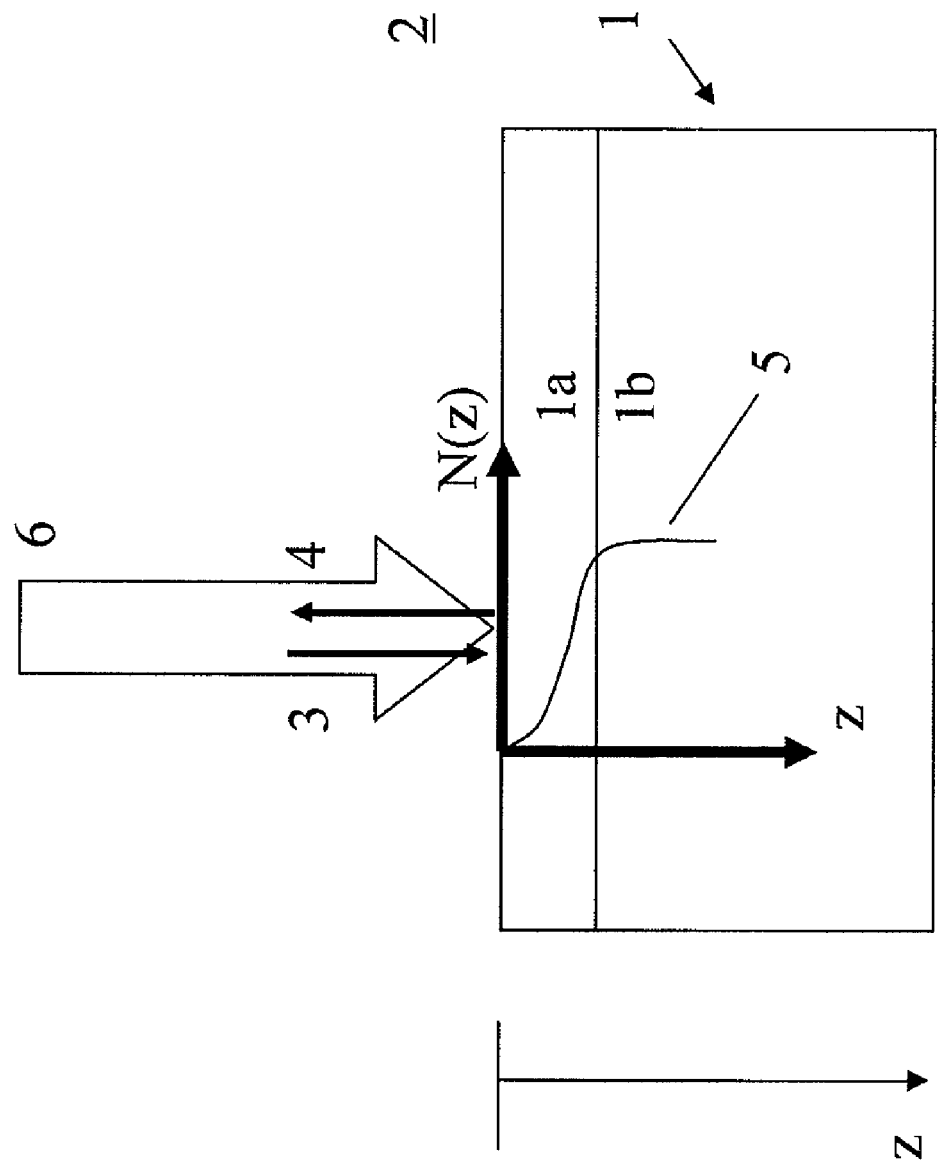
Figure 1: prior art

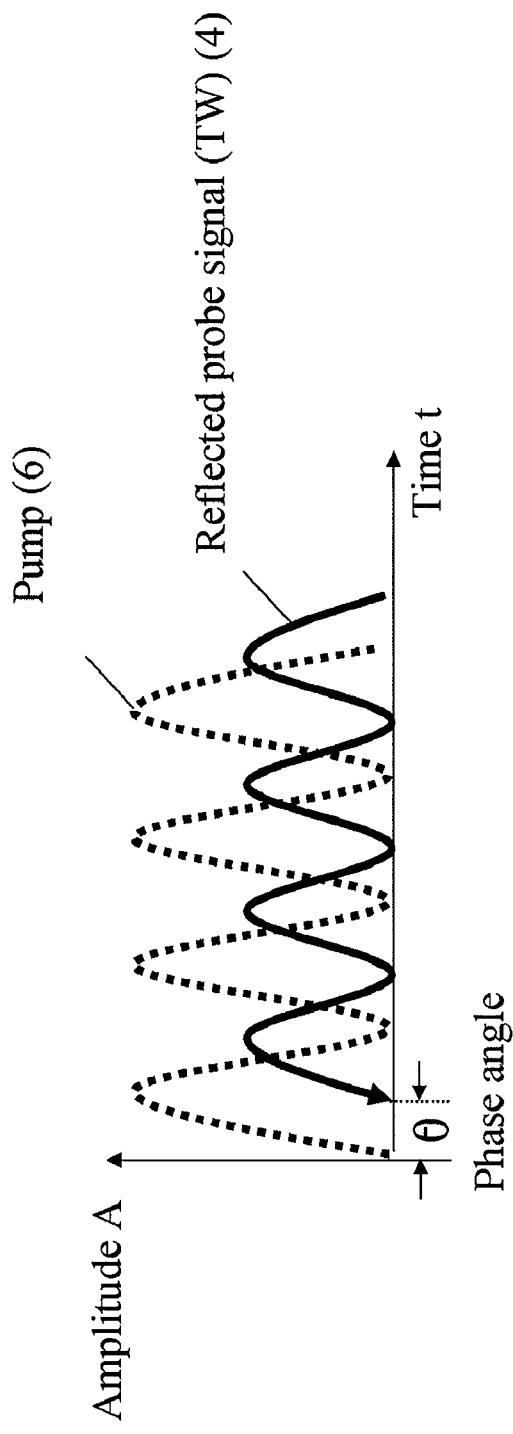
Figure 2a: prior art
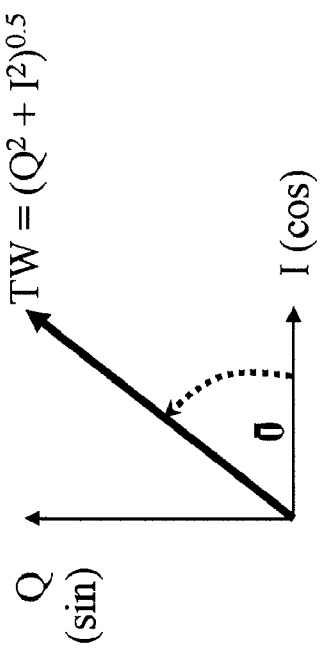
Figure 2b: prior art

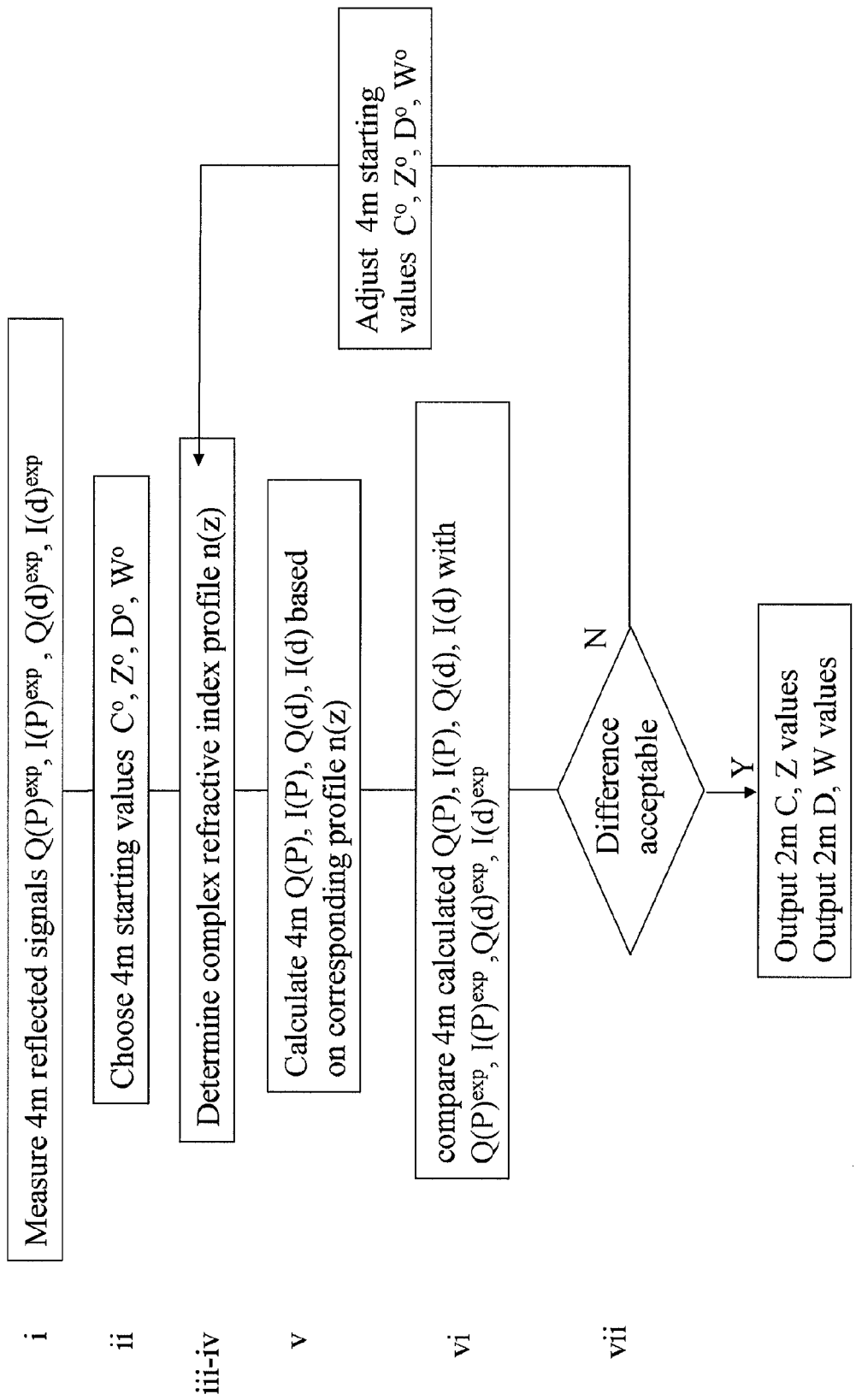

US 7,751,035 B2

METHOD AND DEVICE TO QUANTIFY ACTIVE CARRIER PROFILES IN ULTRA-SHALLOW SEMICONDUCTOR STRUCTURES

CROSS REFERENCE TO RELATED APPLICATIONS

This application is a continuation of PCT Application No. PCT/EP06008709, filed Sep. 7, 2006, which is incorporated by reference hereby in its entirety.

BACKGROUND OF THE INVENTION

1. Field of the Invention

The present invention relates to non-destructive optical measurement techniques, apparatus and systems for determining the active carrier profile in semiconductor layers. In particular it relates to using of optical energy to create charge carriers in these semiconductor layers and to probe changes in reflectivity created by these charge carriers as function of the depth in the semiconductor layer where these carriers agitate.

More particularly, the present invention relates to methods, apparatus and systems for extracting the active carrier profile in ultra shallow junctions in a particular semiconductor substrate. In particular it relates to extracting such information from a single set of measurements on a semiconductor substrate. The present invention also relates to devices and software for carrying out such methods.

2. Description of the Related Technology

In semiconductor processing, methods are required for the determination of properties of semiconductor materials, such as Si, SiGe, GaAs, . . . , and their dependence on processing conditions. Introducing species into a semiconductor material by, for example, ion implantation can change the properties of the bulk material. Other methods that can change the properties of the bulk material are manufacturing of the substrate, annealing such as for example rapid thermal processing (RTP) or rapid thermal annealing (RTA), etc. In CMOS (Complementary Metal Oxide Silicon) devices for example, it is important to be able to determine the junction depth and profile of the source and drain regions formed in the semiconductor substrate. For advanced high-performance CMOS technologies, it is, for example, crucial to be able to quickly and reliably characterize ultra shallow junctions. Especially, as CMOS structures, such as for example transistors, become increasingly smaller the doping profiles, in particular the active carrier profiles, shrink accordingly. Advanced CMOS structures will have gate lengths less than 50 nm and junction depths less than 70 nm. The exact determination of these profiles becomes more difficult and at the same time more critical. Process conditions need to be optimized in order to obtain the desired junction depth and profile and, hence, to yield the required device characteristics. One of the many crucial issues in fabricating state-of-the-art CMOS transistors is the precise control over the positioning and electrical characteristics of source/drain and extension regions. Besides the currently used low energy ion implantation and fast annealing techniques, much effort is placed in new techniques such as laser annealing (LTA) and low temperature Solid Phase Epitaxial Regrowth (SPER) to achieve higher concentration levels (above solubility) and steeper profiles (smaller thermal budget). Typically small variations in for example temperature or temperature gradient already cause unacceptable changes in for example junction depth.

Various methods exist to investigate the properties of the semiconductor active carrier profile. Some of these techniques, however, are destructive. Presently people use for doping characterization typically a combination of one-dimensional techniques such as Secondary-Ion-Mass-Spectroscopy (SIMS) for the total profile, Spreading-Resistance-Profile (SRP) for the electrically active carrier profile and Four-Point-Probe (FPP) measurement for sheet resistance. SIMS and SRP have the disadvantage that they are off-line techniques, applicable only on small pieces of material. In case of SRP the semiconductor substrate to be characterized is cleaved along a diagonal cleavage line and a two-point electrical measurement is then performed at subsequent positions along this cleavage line. For SIMS the material from the substrate under examination will be locally removed and subjected to further analysis. Furthermore a measurement on one specific position on a wafer takes about a day taking into account the sawing, preparation sample, measurement, calculation, etc. Conventional FPP can quickly measure whole wafers, but does not give any profile information and still requires rather large analysis areas, typically larger than 1 $mm^2$. Furthermore, probe penetration leads to unreliable results on ultra-shallow profiles, particular when less than <30 nm deep. Recently some new promising techniques have emerged. For example two-dimensional carrier imaging techniques such Scanning-Capacitance-Measurement (SCM) or Scanning-Spreading-Resistance-Microscopy (SSRM), but one still needs small pieces for the measurements, a complicated and critical sample preparation is required and the depth resolution still needs improvement (5-10 nm). Furthermore these two-dimensional techniques depend critically on the availability of more reliable one-dimensional calibration profiles.

Other known techniques are non-destructive such as, for example, the Carrier Illumination (CI) technique, as disclosed in U.S. Pat. No. 6,049,220 and U.S. Pat. No. 6,323,951, and the Therma Probe (TP) technique, also called Thermawave technique or thermal wave technique as disclosed in "Non-destructive analysis of ultra shallow junctions using thermal wave technology" by Lena Nicolaides et al. in Review of Scientific Instruments, volume 74, number 1, Jan. 2003. All publications are hereby incorporated by reference in their entirety.

Referring to FIG. 1, in CI, TP and similar non-destructive optical techniques, typically two lasers (6, 3) are used. A first laser (6) is a focused pump laser or generation laser, generating a "pump" laser beam or generation beam. The first laser operates at a fixed wavelength, with an energy larger than the band gap of the semiconductor material under study. This pump laser (6) is used to generate an excess carrier profile in the bulk of the semiconductor material under investigation, giving rise to a depth dependent index of refraction of the material. Depending on the modulation frequency of the pump laser a quasi-static excess carrier profile is generated wherein the variation in the number of excess carriers is in phase with the variation of the pump laser or a dynamic excess carrier profile is generated wherein the variation in the number of excess carriers is not in phase with the variation of the pump laser. For the CI the frequency of the pump laser is in the kilo Hertz range, typically 1 kHz, resulting in quasi-static excess carrier profile, while for the TP the frequency of the pump laser is typically in the mega Hertz range, typically at about 1 MHz, resulting in a dynamic excess carrier profile dependent on the total carrier level as the lifetime of the excess carriers is inverse proportional to the total carrier level. The thus generated excess carriers distribute themselves in the semiconductor material according to a profile which is defined as the excess carrier concentration and is expressed in number of carriers per $cm^3$ exceeding the level of carriers present within the semiconductor substrate without stimulation, this latter being labeled as the background carrier concentration or profile, e.g. in the absence of illumination. This background carrier concentration is dependent on the concentration of dopant atoms. Specifically, the excess carrier concentration changes from zero outside a surface of the semiconductor material to a finite value inside the semiconductor material. This change in excess carrier concentration results in a steep increase in the concentration of excess carriers at the surface of the semiconductor substrate. This steep increase of the excess carriers concentration at the interface between the semiconductor material under study and its surroundings, e.g. air, will be labelled as the near-surface component which will result in a near-surface component. As the depth z, which is defined from the illuminated surface of the semiconductor substrate into the semiconductor substrate, increases, the excess carrier concentration changes proportionally to the change in the concentration of dopant atoms or to the presence of recombination centers. For example, in some cases, the dopant concentration rises, but in other cases the dopant concentration dips first and then rises, depending on the detailed shape of the doping profile.

A reflected signal is generated by illuminating the optically stimulated semiconductor material with a second "probe" laser (3), generating a probe laser beam or probe beam, which may also be labeled analyzer beam, having a fixed wavelength which is typically higher (in case of CI) or lower (in case of TP) than the fixed wavelength of the "pump" laser. This probe laser beam will be reflected at the sample surface and/or at any region with a large change in the index of refraction proportional to the excess carrier profile, as is illustrated in FIG. 1. Reflected light (4) from the second laser (3) provides a signal, which is dependent on the profile depth. Currently reflected signals are converted to a value representative of junction depth using an algorithm developed through extensive correlation of CI or TP measurements with SRP measurements on a wide range of implants. FIG. 1 shows a semiconductor substrate (1), a pump laser beam (6) and a probe laser beam (3) impinging from the surroundings (2) on the semiconductor substrate (1). The incident probe laser beam (3) and the reflected probe laser signal (4) are indicated by respectively arrows (3) and (4). The semiconductor substrate (1) in this illustrative example comprises a doped layer (1a) formed on an undoped or lower doped region (1b). The substrate (1) can be formed by depositing an in-situ doped layer (1a) on top of layer (1b), yielding a uniform doping profile over region (1a) or can be formed by implanting dopants into the substrate (1), yielding a doped region (1a) and an undoped region (1b). By using e.g. ion implantation for implanting dopants into the substrate (1), any kind of doping profile can be obtained depending on the choice of implant species, the energy and implantation dose used. Layer 1a can be doped with a dopant of the same or the opposite type of dopant used to dope the underlying layer 1b. In FIG. 1, the excess carrier profile N(z) as function of depth z into the substrate (1) is also shown, indicated by graph 5. The probe laser beam (arrow 3) will be reflected, thus generating the reflected probe laser signal (arrow 4) at various positions on the semiconductor substrate (1). For example, the probe laser beam (3) may be reflected at the surface, yielding a surface component in the reflected probe laser signal (4). It may also be reflected by a change in the excess carrier profile which can occur at the surface, yielding a near-surface component, or at the interface between the doped part (1a) and undoped part (1b) on the gradient of N(z), yielding a bulk (or interface) component. Laser beams from both lasers, pump laser (6) and probe laser (3), are superimposed onto each other and may contact the semiconductor substrate (1) in the same or in a different area. Typically, both lasers are in a fixed measurement set-up and both incident laser beams have a direction perpendicular to the wafer surface or substrate surface, meaning incident at a zero angle relative to the wafer surface normal.

As indicated above, TP and CI use two lasers, a pump (830 nm for CI and 790 nm for TP) and a probe laser (980 nm for CI and 670 nm for TP). For activated structures the role of the pump laser is to generate a sufficient amount of excess carriers (typically more than $10^{18}/cm^3$) varying with depth, such that the corresponding variations of the refractive index become visible for the probe laser and hence a sufficient contrast is obtained. The final excess carrier profile is a convolution of the generation, absorption and recombination mechanisms in the semiconductor substrate (1), where among others Auger recombination is strongly dependent on the underlying dopant profile. The latter contribution to the measured signal is called the electronic component. In addition there is a thermal component to account for, due to the local heating (5-15° K.) underneath the lasers caused by the high local energy densities (800 kW/cm²). The electronic and thermal components have opposite signs. For activated source/drain implants the amount of excess carriers in the highly doped region typically is rather low, typically by one order of magnitude relative to the substrate, to start rising steeply in the "junction" region towards the substrate level. Consequently, a significant part of the total reflected probe signal comes from close to the junction. This part of the signal is referred to as the interface component $E_{interface}$. Important to note is that this "junction" is not directly related with the metallurgical or electrical junction, but with a depth on a SIMS profile corresponding with a dopant level of about $10^{18}$ at/cm³, i.e. the excess carrier level in the substrate. The cosine shape of the reflected signal versus junction depth is due to the depth dependent constructive or destructive interference of the interface component with the reflection of the probe laser with the sample surface, called the surface component $E_{surface}$.

Due to the small size of the signals, typically 0.001% of reflection on pure silicon, a modulated pump laser needs to be used in combination with "lock-in" techniques. CI uses a low modulation frequency in the kilohertz range, typically 1 kHz, which corresponds to a quasi-static operation mode and the excess carrier profile is able to follow the modulation frequency of the pump laser. TP uses a high modulation frequency in the megahertz range, typically 1 MHz, causing wave formation and the excess carrier and temperature profiles will be out of phase with the pump signal as illustrated in FIG. 2a. A phase difference $\Phi$ exists between the pump signal (6) and the probe signal reflected (4) by the excess carriers and the induced temperature difference. In fact in practice one records respectively the in-phase ($I=A.\cos(\phi)$) and quadrature ($Q=A.\sin(\phi)$) components as shown in FIG. 2b, where A is the amplitude of the reflected signal (4).

For not-activated structures, a correlation between the reflected signals with the implanted dose has been established. As such, commercial TP/CI tools are being used in many important microelectronics companies and labs all over the world for the in-line qualitative monitoring of the reproducibility of implant and anneal cycles. Currently there is a tendency to use these qualitative analytical techniques in a more quantitative way. For an unknown sample, the depth where the interface signal originates from can, for a fixed pump laser power and corresponding excess carrier level, in principle be determined based from earlier established correlation curves plotting the amplitude $E_r$ of the CI signal or the Q component of the TP signal versus SIMS at the actual injection depth resulting in cosine-like shaped curves. Such correlation curves for CVD (chemical vapor deposition) grown layers indicate an achievable depth resolution of 1-2 Angstrom. A major problem with these correlation curves, however, is that they are dependent on many factors such as used implant species, type of implant/anneal process, etc. introducing a large uncertainty about which correlation curve(s) to use for an unknown sample.

SUMMARY OF CERTAIN INVENTIVE ASPECTS

In one aspect, the present invention relates to an optical measurement method to determine an active carrier profile of a semiconductor substrate comprising generating m measurement points, each measurement point comprising two independent measurement signals, and correlating these m measurement points with m profile points, each profile point comprising an active carrier concentration and the corresponding depth, with m being an integer value. This inventive aspect allows correlating 2 m independent measurement values obtained using a non-destructive optical measurement technique with 2 m independent carrier profile values.

In another aspect, the present invention relates to an apparatus for determining an active carrier profile of a semiconductor substrate comprising an illumination device, comprising a means for creating excess carriers, and a probe laser for impinging a laser beam, at least partially reflected by the excess carriers, on the semiconductor substrate, thus generating a reflection signal, means for varying the depth at which the reflection signal originates, means for measuring the reflection signals, storing means for storing m measured reflection signals, each reflection signal comprising two independent signals, and means for correlating the m measured reflection signals with m profile points, each profile point comprising an active carrier concentration and the corresponding depth, with m being an integer value. The means for varying the depth at which the reflection signal originates can comprise varying the power of the generation laser, varying the time during which each reflection signal is measured or varying the distance (offset) between the means for generating excess carriers and the probe laser. By varying the depth from which the measured signal originates the active carrier profile can be scanned.

In another aspect, the present invention also relates to an optical measurement method to determine simultaneously an active carrier profile and at least one other material parameter profile of a semiconductor substrate, where the other material parameter can be defect related thereby impacting the recombination process of the excess carriers, the method comprising: generating 2 m measurement points, each measurement point comprising two independent measurement signals, and correlating these 2 m measurement points with 2 m profile points, each profile point comprising an active carrier concentration with its corresponding depth and a second parameter concentration with its corresponding depth, whereby m is an integer value. Hence this inventive aspect allows correlating 4 m independent measurement values obtained using a non-destructive optical measurement technique with 4 m independent parameter profile values.

In another aspect, the present invention also relates to an optical measurement method to determine simultaneously an active carrier profile and multiple material parameter profiles of a semiconductor substrate, where the material parameter can be defect related, thereby impacting the recombination process of the excess carriers the method comprising generating [n.k] data profiles, whereby each data profile comprises m measurement points, each measurement point comprising 2 independent measurement signals. These [n.k].m measurement points are correlated with up to [n.k].m profile points of the material parameter profiles, each profile point comprising a concentration value with its corresponding depth value. Hence this inventive aspect allows correlating [n.k] [m.2] independent measurement values obtained using a non-destructive optical measurement technique with [n.k] [m.2] independent parameter profile values. The numbers m, n, k correspond to the values set for the depth varying means, being respectively the power of the pump laser beam, the offset between the pump laser beam and the probe laser beam and the measurement timed during which the reflected probe signal is measured. The numbers m, n, k are integers.

In yet another aspect, the present invention relates to an apparatus for determining an active carrier profile and a second parameter profile, e.g. defect/recombination profile, of a semiconductor substrate comprising an illumination device comprising a means for creating excess carriers, and a probe laser for impinging a laser beam, at least partially reflected by the excess carriers, on the semiconductor substrate, thus generating a reflection signal, means for varying the depth at which the reflection signal originates, means for measuring the reflection signals, storing means for storing 2 m measured reflection signals, each reflection signal comprising two independent signals, and means for correlating the 2 m measured reflection signals with 2 m profile points, each profile point comprising an active carrier concentration with its corresponding depth and a second parameter concentration with its corresponding depth, whereby m is an integer value. The means for varying the depth at which the reflection signal originates comprises the power of the generation laser, the time during which each reflection signal is measured and/or the distance (offset) between the means for generating excess carriers and the probe laser. By varying the depth from which the measured signal originates the active carrier profile and the other parameter profile can be scanned.

In still another aspect, the present invention relates to an apparatus for determining an active carrier profile and multiple other material parameter profiles, the material parameter influencing the index of refraction of the material, through for example changes in the temperature and excess carrier profile, the apparatus comprising an illumination device comprising a means for creating excess carriers, and a probe laser for impinging a laser beam, at least partially reflected by the excess carriers, on the semiconductor substrate, thus generating a reflection signal, means for varying the depth at which the reflection signal originates, means for measuring the reflection signals, storing means for storing [n.k].m measured reflection signals, each reflection signal comprising two independent signals, and means for correlating the [n.k].m measured reflection signals with [n.k].m profile points, each profile point comprising a level value, e.g. concentration, speed, temperature, with its corresponding depth. The means for varying the depth at which the reflection signal originates comprises the power of the generation laser, the time during which each reflection signal is measured and/or the distance (offset) between the means for generating excess carriers and the probe laser. By varying the depth from which the measured signal originates the active carrier profile and other material parameter profiles can be scanned.

In another aspect, the present invention also relates to a computer program product for executing the extraction methods according to one inventive aspect when executed on a computer device.

One inventive aspect also relates to a machine-readable data storage device storing the computer program product for executing the methods according to the invention when executed on a computer device.

BRIEF DESCRIPTION OF THE DRAWINGS

FIG. 1 is an illustration of the conventional Therma Probe technique;

FIG. 2 is an illustration of the conventional Therma Probe technique; (a) pump signal (dotted line) and reflected probe signal (solid line) (b) the components Q, I of the reflected probe signal;

FIG. 12 is a flow chart illustrating an extraction method for a complete carrier profile (C, Z) and second parameter profile (D, W) according to an embodiment of the present invention;

DETAILED DESCRIPTION OF CERTAIN INVENTIVE EMBODIMENTS

Figure 3:
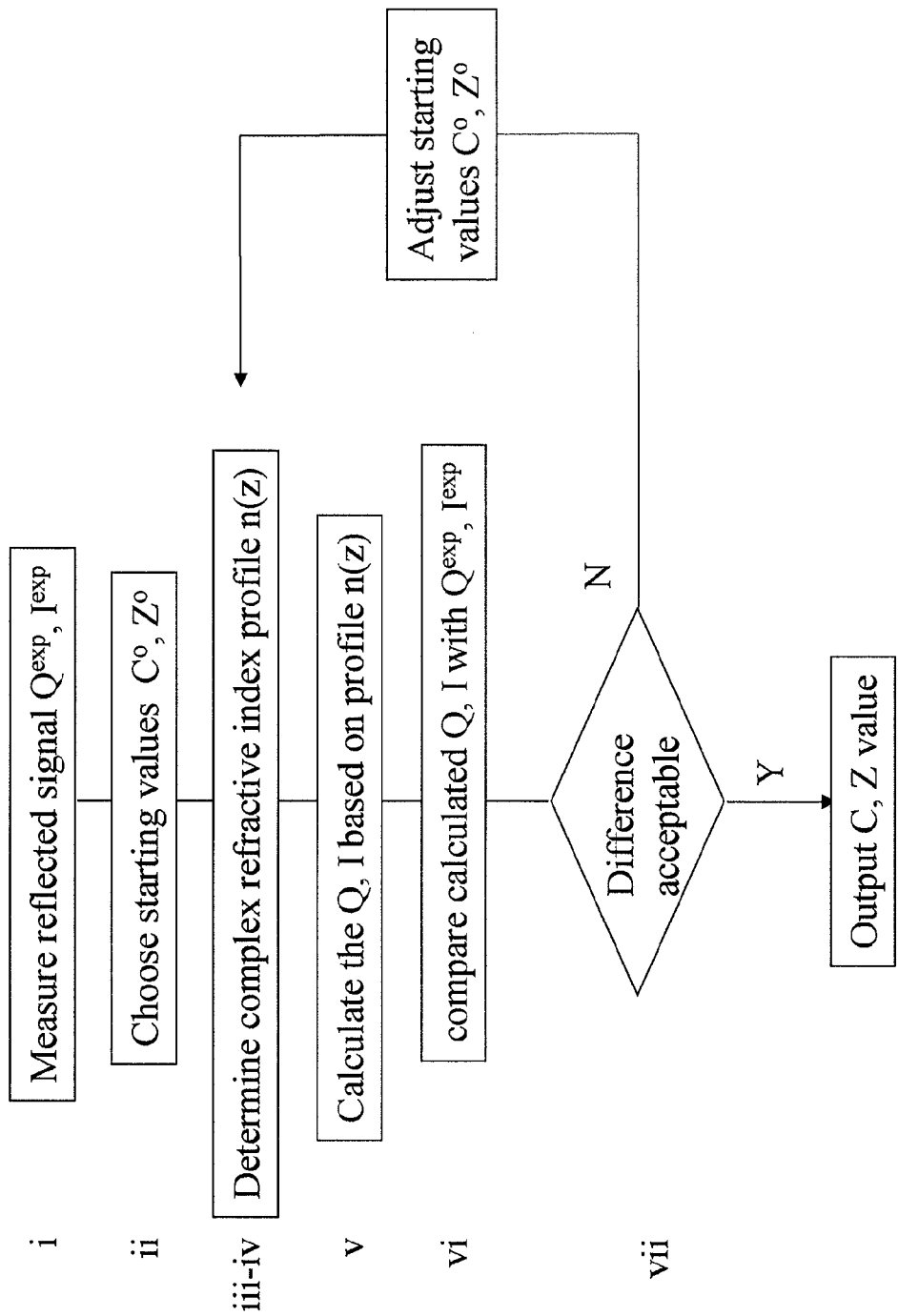
FIG. 3 is a flow chart illustrating an extraction method at one measurement point according to an embodiment of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention. It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B. The invention will now be described by a detailed description of several embodiments of the invention. It is clear that other embodiments according to the invention can be configured according to the knowledge of persons skilled in the art without departing from the true spirit or technical teaching of the invention, the invention being limited only by the terms of the appended claims.

Certain embodiments relate to a non-destructive method, an apparatus or a system to determine at least the active carrier profile for an unknown semiconductor sample, in particular for ultra-shallow semiconductor structures.

Certain embodiments relate to a non-destructive method, an apparatus, or a system to determine, for an unknown semiconductor sample, in particular for ultra-shallow junctions, the profile of the active carriers and the profile of another material parameter, the material parameter influencing the index of refraction of the material, through for example changes in the temperature and excess carrier profile.

Certain embodiments relate to a non-destructive method, an apparatus or a system that allows a quantitative analysis with a high reproducibility of a semiconductor substrate in arbitrary locations on unpatterned and patterned wafers, even in small structures, having an area of less than a few $\mu m^2$.

Certain embodiments relate to a non-destructive method, an apparatus or a system that allows reconstructing at least the active carrier charge profile of an unknown semiconductor substrate underlying the depth dependent reflected signal, without using correlation curves for each measurement point.

In a first aspect of the invention a method to correlate the measurement data with the active carrier profile of the semiconductor substrate under study is disclosed.

When a high frequency (>>1 kHz) modulated pump laser beam is focused on a semiconductor sample both thermal and excess carrier plasma waves are generated. As discussed earlier, in the Therma-Probe technique, a 790 nm "pump" laser beam produces the periodic heating modulated at 1 MHz. A 670 nm "probe" laser beam is collinearly focused on the same spot on the sample surface as the pump laser and measures the periodic changes in the reflectivity of the specimen. In semiconductors, the modulated reflectance signal on the probe beam arises from thermal and electron-hole plasma density related effects. This is because the optical properties of materials are dependent on the temperature and the electron-hole plasma density near the surface of the material. Therefore as the pump laser (6) modulates the temperature and electron-hole plasma density near the specimen surface, the reflectance of the probe beam experiences a corresponding modulation. It is this time-variant component in the probe reflectance signal which gives the reported "TW signal" values. The electric field of the reflected probe laser beam ($E_r$)

can be fully characterized by the amplitude of the modulated reflectance (A) (conventional TW signal) and its phase angle (φ) relative to the original pump laser optical signal (3). Based on the amplitude and phase angle, one can define the in-phase (I) and quadrature (Q) components as defined by the equations:

$$E_r = A e^{i\phi} = A\cos(\phi) + iA\sin(\phi) = I + iQ \quad (1)$$

Hence, one measures basically two independent parameters, either A and φ or I and Q. Having such two independent parameters for each measurement point is a requirement for the unique deconvolution of the active carrier depth profile underlying the depth dependency of the reflected signal.

Figure 4:
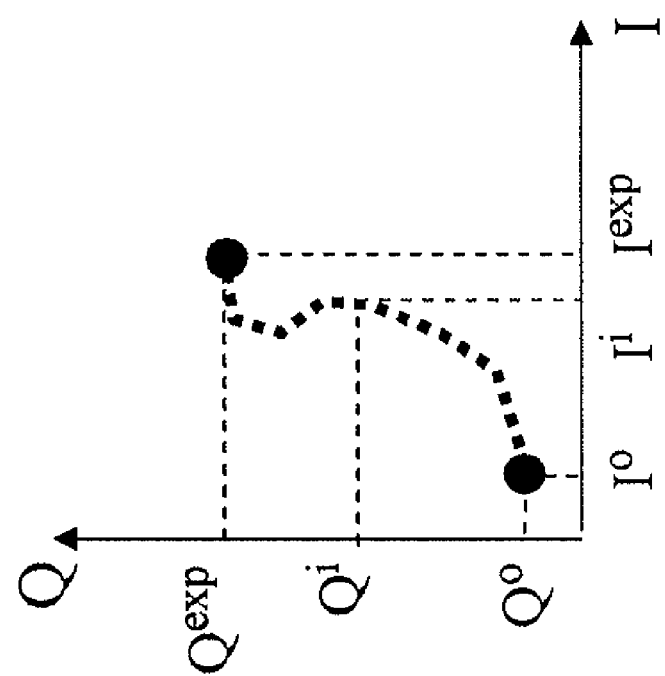
FIG. 4 illustrates the extraction method of FIG. 3.

In case the underlying active dopant depth profile is box shaped (as grown by CVD), i.e. is uniquely characterized by its carrier concentration level (C) and its junction (interface) depth (Z), the following steps, illustrated by FIG. 3, will lead to a unique extraction of these two variables (C, Z) for any unknown box profile from a single TP measurement (Q, I) for a given setting of the measurement tool:

(i) Measure the experimental reflected signal $I^{exp}+iQ^{exp}$ on the unknown structure with a box profile
(ii) Choose carrier concentration and junction depth starting values ($C^0$, $Z^0$) for the unknown variables (C, Z).
(iii) Use a device simulator to calculate the photo-induced in depth varying excess carrier (N(z)) and temperature profile (T(z)) within the doped structure based on the solution of among others the Poisson equation, the current equations and temperature diffusion equations and appropriate physical models involving among others the necessary generation, absorption and recombination models as known in the art.
(iv) Determine the (complex) refractive index profile (n(z)=F(N(z),T(z)) with F a non-linear function) due to the presence of the above-calculated excess carrier (N(z)) and temperature (T(z)) depth profiles, among others based on the application of the Drude model.
(v) Calculate the corresponding (expected) TP signal $I^0+iQ^0$ from multi-layer reflection theory based on the shape of n(z).
(vi) Compare the initially simulated signal $I^0+iQ^0$ with the experimentally recorded $I^{exp}+iQ^{exp}$ signal, determine the error (difference) between both in two-dimensional space by some appropriate mathematical measure and adapt the two independent variables $C^0$ and $Z^0$ in order to improve the initial guess for the unknown carrier concentration C and junction depth Z. The latter can be done by specialized mathematical non-linear problem solvers, which are commercially available.
(vii) Go to step (iii) above and continue this iterative non-linear process until the unique solution (C, Z) has been found. The series of intermediate solutions ($C^i, Z^i$) (until convergence has been reached) can be represented by a non-linear curve in the two-dimensional plane I+iQ or (C,Z) (see FIG. 4). Given the fact that there are only two unknown variables for a box profile, a single TP measurement with its two independent signals Q, I suffice to extract the required characteristics (carrier concentration and junction depth).

Figure 5A:
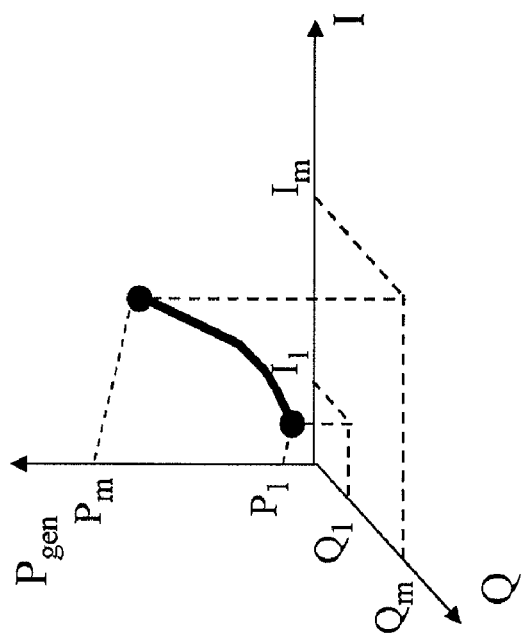
FIG. 5 a illustrates the correlation between (a) measurement curve and (b) active dopant profile of the semiconductor substrate under study according to an embodiment of the present invention.
Figure 5B:
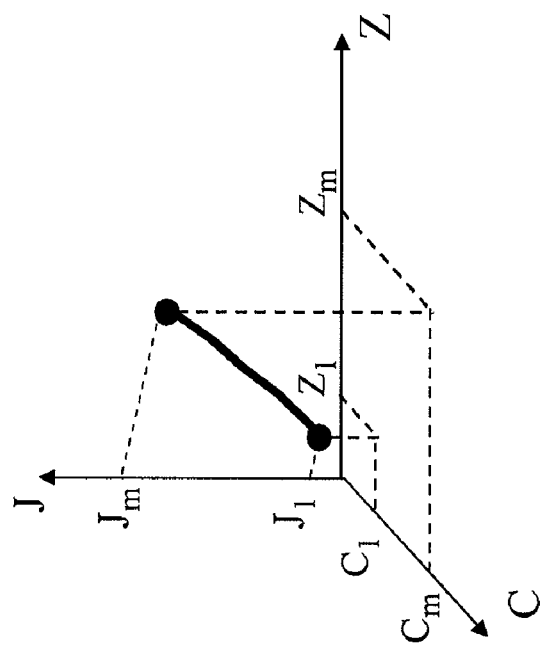

In case the underlying active dopant profile has a more general shape (for example Gaussian) a more general approach is needed. In the latter case the variation in the parameters amplitude (A) and phase angle (φ) (and therefore power), of the probe laser signal reflected by the sample (4) can be plotted as function of a third specific tool parameter: either the applied pump laser (3) power ($P_{gen}$) (power curves), the offset (d) between both laser beams (3, 6) (offset curves), or the time ($t_{meas}$) during which the reflected signal (4) is monitored (charge curves), as these parameters change the depth where the interface signal originates from. Hence by varying these tool parameters the active carrier profile can be scanned over a predetermined depth range. As a result a set of m data points {Q, I} is obtained for every value of these parameters as illustrated by FIG. 5a. The current extraction method thus comprises the generation of 2 m measurement values for m measurement points J.

At each of the m measurement points J, i.e. at each depth measured, the two independent values $Q_j$ and $I_j$ obtained during this measurement are correlated with the two unknown active carrier profile parameters $Z_j$ (depth at position j) and $C_j$ (=carrier concentration at position j) corresponding to that measurement depth. The current extraction method thus comprises correlating the set of 2 m independent measurement values $\{Q_j, I_j\}$ with j: 0→m, with the set of 2 m independent carrier profile values $\{C_j, Z_j\}$ with j: 0→m.

The 2 m unknown values $\{C_j, Z_j\}$ with j: 0→m can be extracted uniquely from the 2 m measured values $\{Q_j, I_j\}$ with j: 0→m, by following the following iterative solution scheme:

(i) Measure the 2 m experimental reflected signals $I_j+iQ_j$, j: 0→m on the unknown structure with a general profile by varying the selected tool parameter.
(ii) Choose carrier concentration and junction depth starting values ($C_j^0$, $Z_j^0$) for each of the 2 m unknown variables ($C_j, Z_j$).
(iii) Use a device simulator to calculate the photo-induced in depth varying excess carrier (N(z)) and temperature profile (T(z)) within the doped structure based on the solution of among others the Poisson equation, the current equations and temperature diffusion equations and appropriate physical models involving among others the necessary generation, absorption and recombination models.
(iv) Determine the (complex) refractive index profile (n(z)=F(N(z),T(z)) with F a non-linear function) due to the presence of the above-calculated excess carrier (N(z)) and temperature (T(z)) depth profiles, among others based on the application of the Drude model.
(v) Calculate the 2 m corresponding (expected) TP signal $I_j^0+iQ_j^0$ from multi-layer reflection theory based on the shape of n(z) and the value of the third tool parameter (pump laser power, beam offset, time) for j: 0→m.
(vi) Compare the initially 2 m simulated signals $I_j^0+iQ_j^0$ with the 2 m experimentally recorded $I_j+iQ_j$ signals, determine the error (difference) between both in 2 .m-dimensional space by some appropriate mathematical measure and adapt the 2 m independent variables $C_j^0$ and $Z_j^0$ for j: 0→m in order to improve the initial guess for the unknown carrier concentration $C_j$ and junction depth $Z_j$ values. The latter can be done by specialized mathematical non-linear problem solvers which are commercially available.
(vii) Go to step (iii) above and continue this iterative non-linear process until the unique solution ($C_j, Z_j$) which defines the complete unknown carrier depth profile has been found. The series of intermediate solutions ($C_j^i, Z_j^i$) (until convergence has been reached) can be represented by a non-linear curve in a 2 m-dimensional plane. Given the fact that there are only 2 m unknown parameter for a general profile to be determined in m different depth locations, m different TP measurements as a function of a third tool parameter with each two independent signals suffice to extract the required characteristics (carrier concentration and junction position for each of the m different depths).

Although in the above extraction procedures numerical methods are used to correlate the reflected signals with the characteristics of the active carrier profile, also analytical formulas can be applied to establish such correlation. Fabian Dortu et al discusses in "Progress in the physical modeling of carrier illumination", Proceedings Eight international workshop on fabrication, characterization and modeling of ultra-shallow doping profiles in semiconductors, Jun. 5-8, 2005, Daytona Beach, Fla., USA, hereby incorporated in its entirety by reference, methods to develop models for correlating reflected signals with the characteristics of an active carrier profile.

For a box shaped profile (two-layer system) characterized by one concentration C and a fixed junction (interface) depth, an analytical expression has been derived relating the reflected signals to the shape of the excess carrier (N(z)) and temperature (T(z)) profile. Considering only the excess carriers this analytical expression is given by:

$$A(C, Z)e^{i\phi(C,Z)} = I(C, Z) + iQ(C, Z) \quad (2)$$
$$= B(N_{surf}(C, Z)e^{i\theta_N(C,Z)} + P_{surf}(C, Z)e^{i\theta_P(C,Z)} +$$
$$\cos(2knZ)(N_{sub}(C)e^{i\psi_N(C)} -$$
$$N_{surf}(C, Z)e^{i\theta_N(C,Z)}) +$$
$$\cos(2knz_{int})(P_{sub}(C)e^{i\psi_P(C)} -$$
$$P_{surf}(C, Z)e^{i\theta_P(C,Z)}))$$
$$= B(N_{surf}(C, Z)e^{i\theta_N(C,Z)} + P_{surf}(C, Z)e^{i\theta_P(C,Z)} +$$
$$\cos(2knZ)N_{int}(C, Z)e^{i\delta_N(C,Z)} +$$
$$\cos(2knZ)P_{int}(C, Z)e^{i\delta_P(C,Z)})$$

with
- $\theta_N, \theta_P$ the phase angle relating to the surface contributions for n- and p-type carriers,
- $\delta_N, \delta_P$ the phase angle relating to the interface contributions for n- and p-type carriers,
- $\Psi_N, \Psi_P$ the phase angle relating to the substrate contributions for n- and p-type carriers,
- Z the (fixed) junction (interface) depth,
- C the (only) carrier concentration level,
- $N_{sub}, P_{sub}$ the modulus of the n-type, p-type substrate excess carrier concentration,
- $N_{surf}, P_{surf}$ the modulus of the n-type, p-type surface excess carrier concentration,
- $N_{int}, P_{int}$ the modulus of the n-type, p-type interface excess carrier concentration
- A the amplitude of the reflected probe signal (4)
- k the probe wave vector in vacuum,
- γ the dependence of refractive index n on temperature
- n the refractive index of the semiconductor substrate (1) under investigation
- B is a proportionality coefficient relating refractive index changes to the excess carrier concentration, e.g. using the Drude theory Formula (2) expresses a non-linear relationship between a Therma-Probe measurement point I+iQ and the corresponding box profile identified by its carrier concentration level and interface depth (C, Z). In these formulas the DC component of the reflected signal, i.e. reflection of the probe signal at the air-semiconductor interface, is already removed and only the AC components are shown.

For the temperature profile T(z) an equation similar to equation (2) can be written:

$$A(C, Z)e^{i\phi(C,Z)} = I(C, Z) + iQ(C, Z) \quad (3)$$
$$= B(T_{surf}(C, Z)e^{i\theta_T(C,Z)} +$$
$$\cos(2knZ)(T_{sub}(C)e^{i\psi_T(T)} -$$
$$T_{surf}(C, Z)e^{i\theta_T(C,Z)}))$$
$$= B(T_{surf}(C, Z)e^{i\theta_T(C,Z)} +$$
$$\cos(2knZ)T_{int}(C, Z)e^{i\delta_T(C,Z)})$$

with
- $\theta_T$ the phase angle relating to the surface contributions of temperature,
- $\delta_T$ the phase angle relating to the interface contributions of temperature,
- $\Psi_T$ the phase angle relating to the substrate contributions of temperature,
- Z the (fixed) junction (interface) depth,
- C the (only) carrier concentration level,
- $T_{sub}$ the modulus of the substrate temperature,
- $T_{surf}$ the modulus of the surface temperature,
- $T_{int}$ the modulus of the interface temperature,
- A the amplitude of the reflected probe signal (4)
- k the probe wave vector in vacuum,
- γ the dependence of refractive index n on temperature
- n the refractive index of the semiconductor substrate (1) under investigation
- B is a proportionality coefficient relating refractive index changes to temperature changes.

Formula (3) expresses a non-linear relationship between a Therma-Probe measurement point I+iQ and the corresponding temperature profile identified by its carrier concentration level C and interface depth Z. In these formulas the DC component of the reflected signal, i.e. reflection of the probe signal at the air-semiconductor interface, is already removed and only the AC components are shown.

In general, a measurement curve in a three-dimensional space is obtained. This space can, for example, be defined by Q, I and $P_{gen}$ (or also A, φ, $P_{gen}$) if power curves are used as discussed further on. The variation of this tool parameter $P_{gen}$ allows varying the "junction" depth, i.e. the depth of main reflection where the main variation of the reflected probe signal stems from a position near to the surface of the semiconductor sample, Z~zero at high pump laser power up to a maximum depth (at low pump laser power). The maximum measurable depth and hence the depth range over which the active carrier profile can be scanned depends on the measurement sensitivity of the tool. Typically this maximum depth will be about $10^{17}$-$10^{18}$/cm$^3$ at low pump laser power. For a single box profile (CVD) in the ideal case a quasi-linear curve will obtained in the (Q, I, $P_{gen}$) space, due to a steady increase in contrast, as the junction depth $z_j$ does not dependent on background excess carrier level due to the large steepness of the dopant profile. The active carrier profile can be reconstructed point by point from the surface towards the bulk of the semiconductor substrate by correlating sequentially (m iterations in two-dimensional space in stead of one iteration in 2 m dimensional space) each set of two measurement values with each set of active carrier profile values using the iterative procedure explained above or formula (2) in case of box profiles.

Alternatively one can start off with the lowest power value for $P_{gen}$ corresponding to the deepest measurable point of the active carrier profile. The active carrier profile can be reconstructed point by point from the bulk towards the surface of the semiconductor substrate by correlating each set of two measurement values with each set of active carrier profile values using the procedure explained above or formulas (2) in case of box profiles.

Alternatively all unknown 2 m variables, i.e. the carrier level $C_j$ and their corresponding depths $Z_j$ at m different positions, are correlated simultaneously based on the 2 m available measurement values, i.e. $Q(P_{gen,j})$ and $I(P_{gen,j})$ for $j=1, \ldots, m$ using known numerical analytical techniques, e.g. matrix calculation, allowing the inversion of a large number (k=50-100) of complex, non-linear equations simultaneously.

Whereas in the previous reconstruction methods no calibration of the obtained measurement curve in the three-dimensional space Q, I and $P_{gen}$ is done, preferably the first measurement point is calibrated. Variations in the tool parameters, such as diameter of the pump laser beam (6), the actual power level etc will cause an offset of the measurement results even when the measurement is repeated on the same semiconductor substrate (1).

It is known that the variation of junction depth in Boron doped single box profiles generates a cosine correlation curve for the Q signal versus SIMS depth. The position of this correlation curve is, however, dependent on the concentration level as it has impact on the surface component. Therefore the first data point of the m data points is preferably calibrated using Q,I signals obtained on substrates having known active carrier profile. T. Clarysse, et al discloses in "Towards non-destructive carrier depth profiling", Proceedings Eight international workshop on fabrication, characterization and modeling of ultra-shallow doping profiles in semiconductors, Jun. 5-8, 2005, Daytona Beach, Fla., USA, p. 38, hereby incorporated in its entirety by reference a method to determine for one given measurement point, i.e. for one pair of Q-I values at a given tool setting, the corresponding concentration N and junction depth Z using two sets of correlation curves. This method can be used to calibrate the first measurement point.

Alternatively together with the semiconductor substrate under study a set of calibration samples having a known active carrier profile is measured. This set of calibration samples comprises at least one calibration sample. Typically these calibration samples have a box-like profile, each with a different peak concentration and junction depth. By simultaneous solving the non-linear equations for both the substrate under study and the calibration samples for the first value of the tool parameter, the unknown tool variations can be eliminated and the first point of the active carrier profile can be obtained.

From this calibrated point onwards the active carrier profile can be reconstructed by correlating the measurement values with t active carrier profile values as discussed in the foregoing paragraphs.

In a second aspect of the invention various methods to obtain 2 m independent data values $(Q_j, I_j)$ at each measurement point j with j: 0→m and m being an integer value, is disclosed. By varying the setting of a tool parameter the depth where the interface signal originates is changed and hence the active carrier profile can be scanned.

Figure 7:
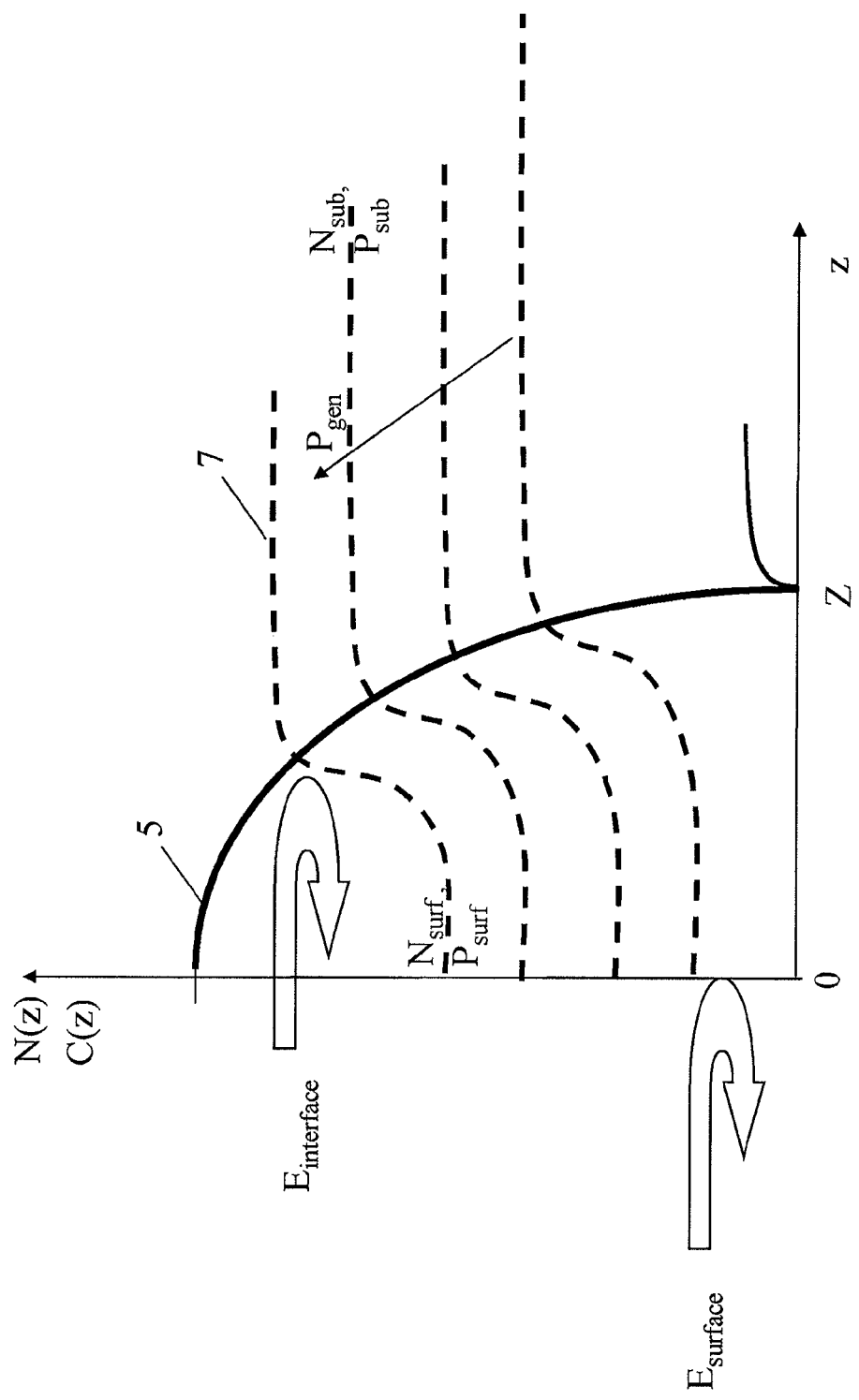
FIG. 7 illustrates one way of scanning the active dopant profile C(z) by varying the power of the probe signal (3)

In a first embodiment of the invention the power of the pump laser (6) is varied while the offset between the probe laser (3) and the pump laser (6) and the time during which each of the m measurements is performed are kept constant. State-of-the art TP systems are modified to allow the increase and decrease of the pump laser power. By enabling the variation of the pump laser in both directions a large enough dynamic range can be obtained as illustrated by FIG. 7. Here for each setting of the tool parameter $P_{gen}$ corresponding excess carrier profiles (7) are generated which intersects with the doping profile (5). Also shown in FIG. 7 are the reflection of the probe signal at this intersection $E_{interface}$ and the reflection at or near the surface $E_{surface}$. This tool parameter variation will result in a three-dimensional measurement curve, which can be represented by: $Q(P_{gen,j})$, $I(P_{gen,j})$ where $P_{gen}$ is the pump laser power as illustrated by FIG. 5a.

Figure 8:
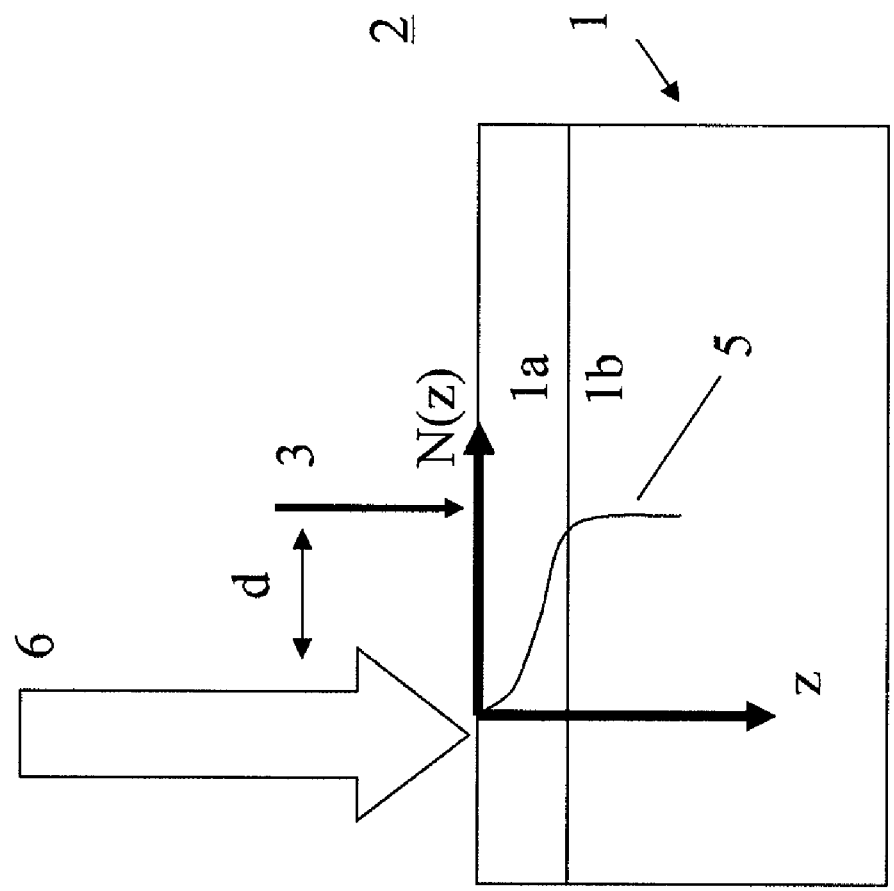
FIG. 8 illustrates another way of scanning the active dopant profile C(z) by varying the offset d between the pump laser (6) and the probe laser (3)

In a second embodiment of the invention the spacing between the probe laser (3) and the pump laser (6) is varied as illustrated by FIG. 8. The power of the probe signal (3) and the time during which each of the m measurements is performed are kept constant. By varying the offset (d) between the probe (3) and pump (6) laser beams a measurement curve in a three-dimensional space Q, I and d is obtained. A large offset d corresponds to almost no excess carriers and therefore little or no signal. A small or zero offset, i.e. both laser beams (3, 6) impinge on substantially the same spot on the semiconductor substrate (1), corresponds to a maximum number of excess carriers and therefore a high signal. When the fixed pump laser power is high enough, one can vary the internal excess carrier level and therefore the origin of the interface component by increasing the beam offset d. The state-of-the-art TP systems are modified to allow changing the beam offset over a range, typically larger than a few micrometers even up to several millimeters.

Figure 6:
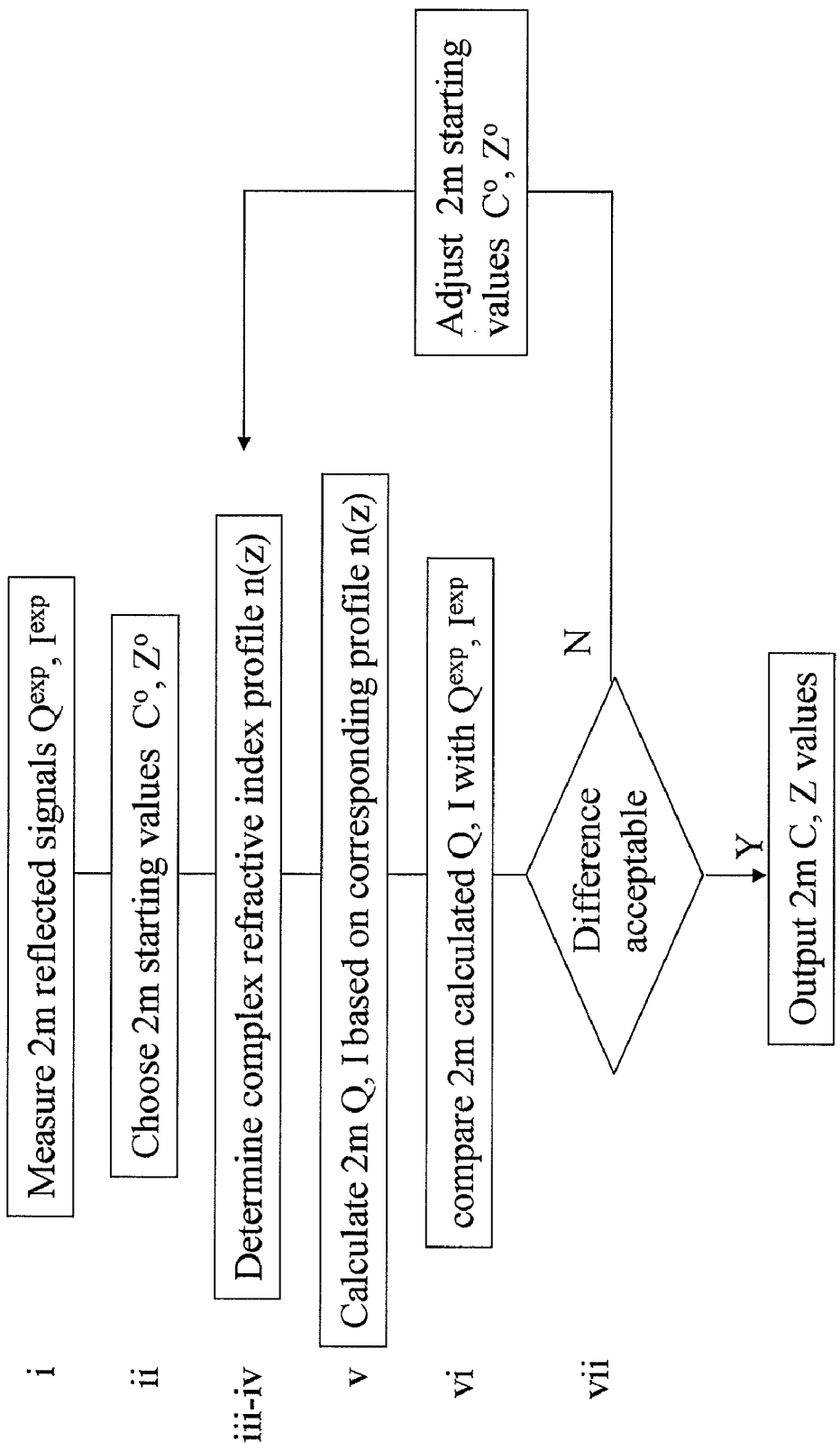
FIG. 6 is a flow chart illustrating an extraction method for a complete carrier profile according to an embodiment of the present invention.
Figure 9:
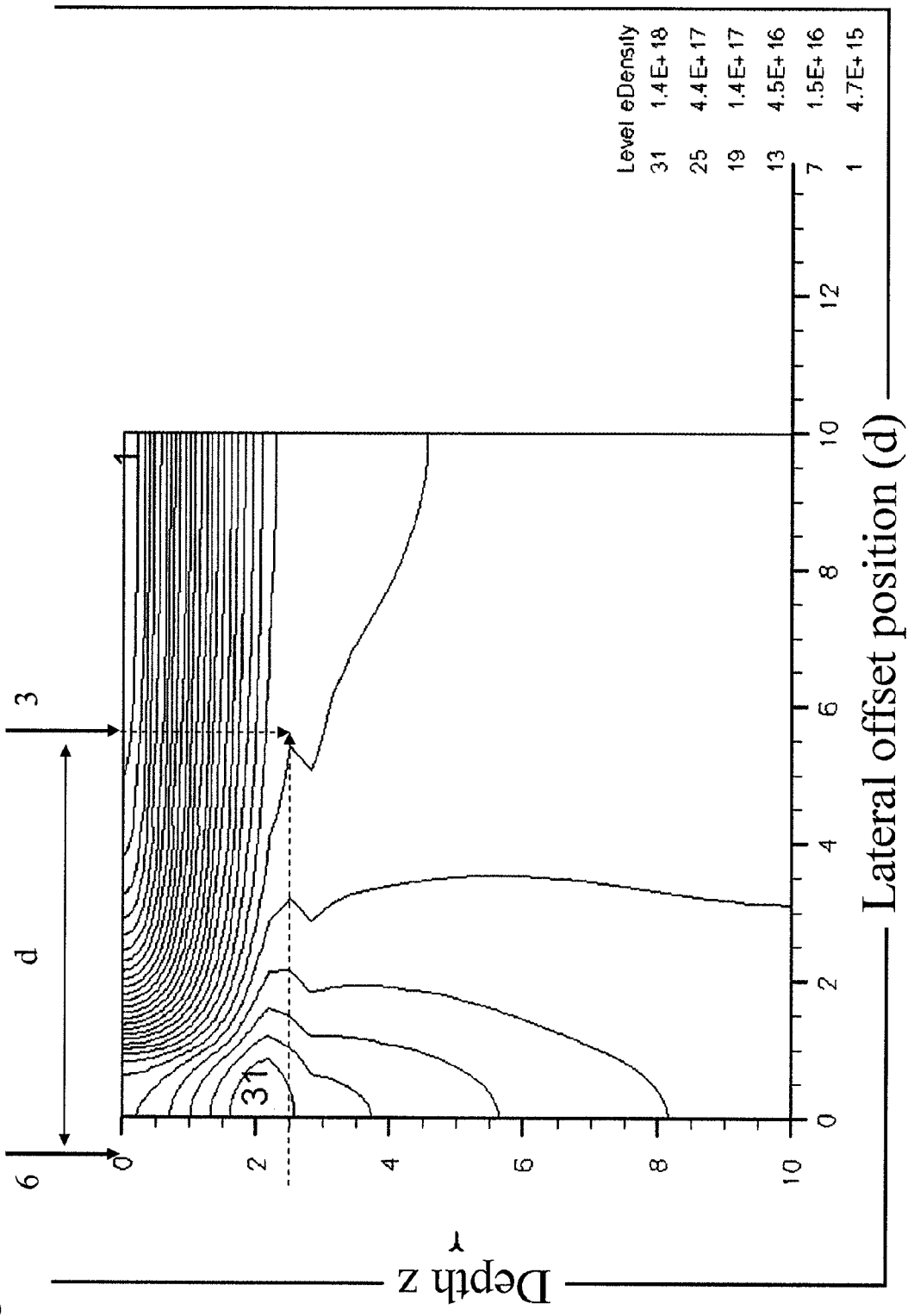
FIG. 9 represents a contour plot of concentration of excess carrier originating from different depth z in the substrate (1) as function of the offset (d) between the pump laser (6) and the probe laser (3)

FIG. 9 represent a contour plot of excess carrier concentration as function of depth z into the substrate and offset (d) between pump laser (6) and probe laser (3). These counter lines are obtained using the method illustrated by FIG. 6 and FIG. 8. The dopant profile considered was Gaussian shaped. For each offset (d) the corresponding value of each contour line indicates the number of excess carriers generated at the depth z and influencing the reflectance properties of the substrate at the chosen position d of the probe laser (3) as indicated by the horizontal and vertical dotted lines. At large offset values d the contribution of excess carriers originating from deep in the substrate will dominate the reflectance of the probe signal (3). Thanks to the lower dopant concentration the lifetime of such excess carrier will be sufficiently long to allow diffusion of these excess carriers over larger distance.

Figure 10:
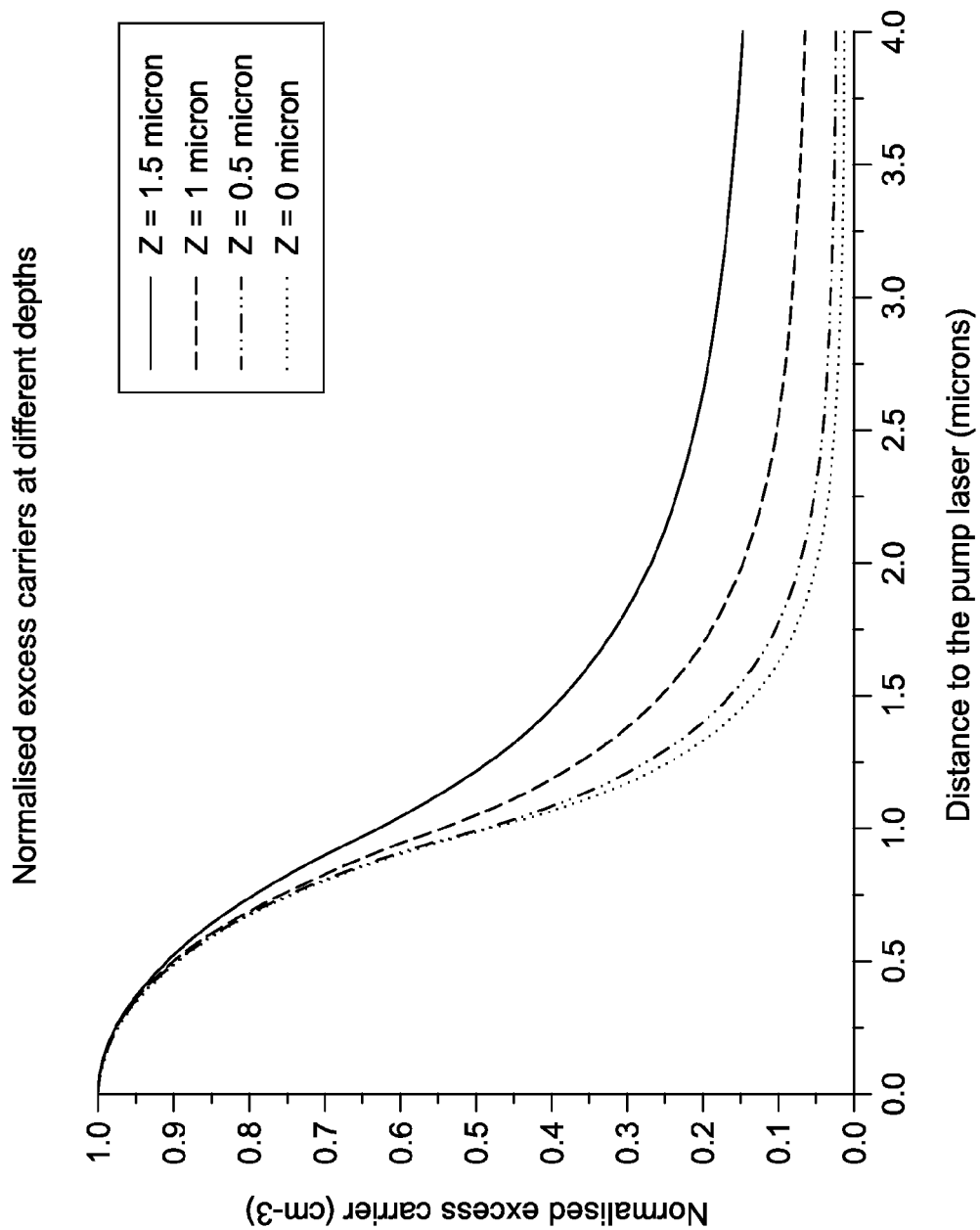
FIG. 10 represents lateral excess carrier concentration at different depths z in the substrate (1) as function of the offset (d) between the pump laser (6) and the probe laser (3) for a Gaussian shaped dopant profile.

FIG. 10 represents the excess carrier concentration originating from a given depth z in the substrate (1) as function of the offset (d). These curves are obtained using the method illustrated by FIG. 6 and FIG. 8. These curves are plotted for four values of the depth z: z=0 micron corresponding to excess carriers generated at the impingement point of the pump laser (3), z=0.5 micron, z=1.0 micron and z=1.5 micron. The excess carrier concentration is normalized relative to the value at z=0. The dopant profile considered was Gaussian shaped. Excess carriers with a short lifetime, i.e. originating from a higher doped part of the substrate which is nearer to the surface of the substrate, will only be of relevance for reflectance in area's close to the pump laser (3).

Figure 11:
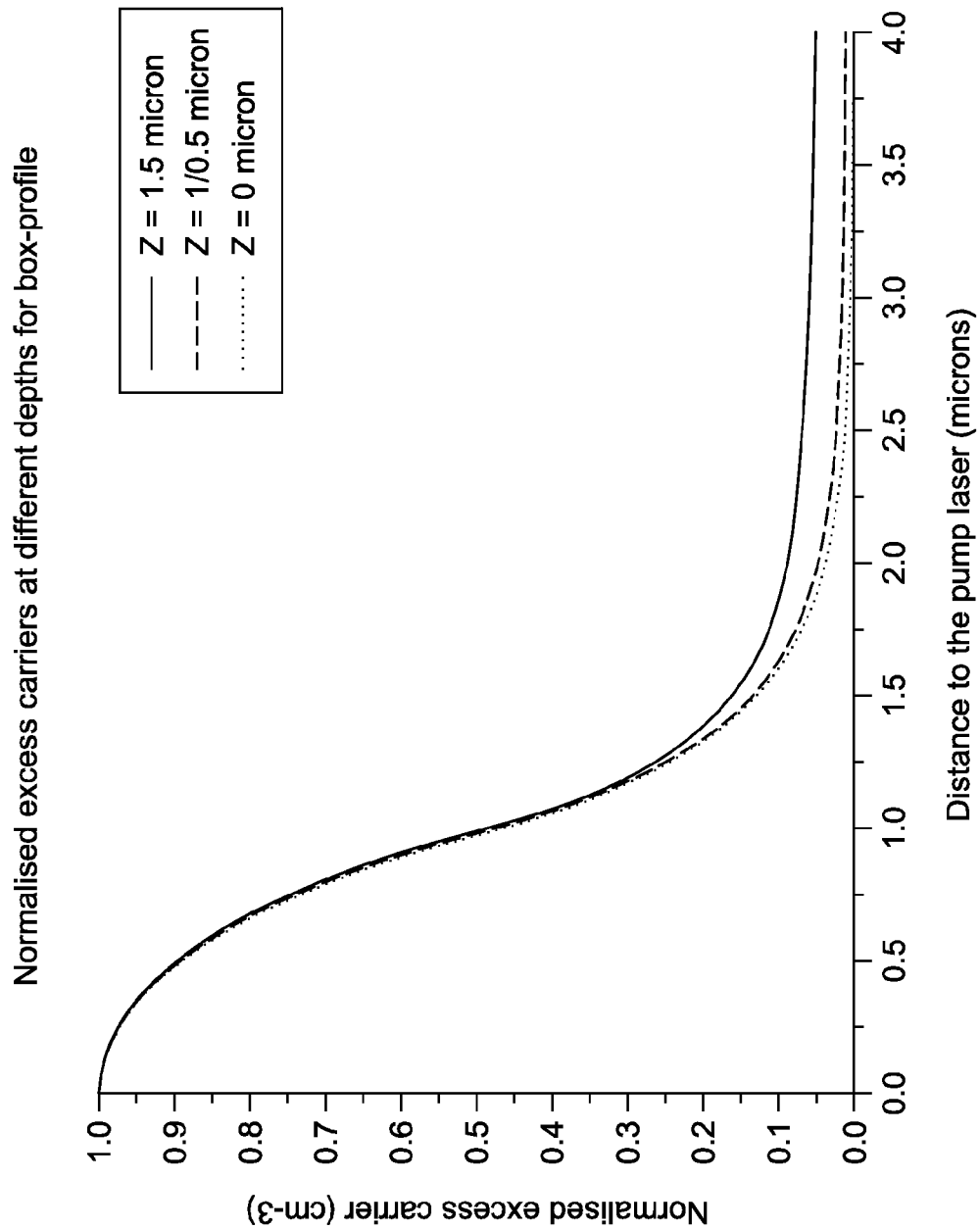
FIG. 11 represents lateral excess carrier concentration at different depths z in the substrate (1) as function of the offset (d) between the pump laser (6) and the probe laser (3) for a box-shaped dopant profile.

FIG. 11 represent the excess carrier concentration originating from a given depth z in the substrate (1) as function of the offset (d). These curves are obtained using the method illustrated by FIG. 6 and FIG. 8. These curves are plotted for four values of the depth z: z=0 micron corresponding to excess carriers generated at the impingement point of the pump laser (3), z=0.5 micron, z=1.0 micron and z=1.5 micron. The excess carrier concentration is normalized to the value at z=0. The dopant profile considered was box shaped, meaning that the dopant concentration is substantially constant at a value $C_j$ until the junction dept $Z_j$. Excess carriers originating from different depths in this box profile will therefore have substantially the same lifetime and diffuse over substantially the same lateral distance. This can be seen in FIG. 11 by the fact that curves corresponding to z=0, 0.5 and 1 um substantially coincide over several microns offset (d).

In a third embodiment of the invention the period $t_{meas}$ during which the reflected probe signal (4) is observed is varied while the power of the probe signal (3) and the offset between the probe laser (3) and the pump laser (6) are kept constant. The measured signals Q, I are time dependent, i.e. a strong non-linear increase is observed between the measured signals Q, I as function of the measurement time $t_{mea}$, probably due to injection of carriers from the semiconductor substrate into a dielectric layer, e.g. a silicon oxide layer, covering the surface of this semiconductor substrate (1). Typically a saturation level of the measured signals Q, I is reached after about 1000 seconds, while the recovering time may be weeks. Plotting the independent signals Q, I versus time gives a measurement curve in a three-dimensional space Q, I and $t_{meas}$ is obtained.

Although in the above three embodiments only one tool parameter is varied to perform the m measurements, a person skilled in the art will realize that a combination of tool parameters settings can be used to generate the 2 m measurement values. One can for example vary the power of the probe laser (3), thereby keeping measurement time $t_{meas}$ and offset d constant, in order to perform some of the m measurements, while afterwards for example the offset d is varied, thereby keeping measurement time $t_{meas}$ and probe laser power constant, to perform some other of the m measurements. Optionally the settings of two or more tool parameters can be varied from one measurement to another measurement in order to generate the m measurement points.

In a third aspect of the invention, at least two independent profiles, i.e. the active dopant profile and a second parameter such as the defect density/recombination rate profile, is extracted. The methods disclosed in the previous aspects of the invention can be applied to generate a sufficient number of measurement points and to correlate these measurement points with the profiles to be extracted.

For any shape of both profiles, for example Gaussian shaped profiles, the variation in the power parameters amplitude (A) and phase angle (phi) of the probe laser signal reflected by the sample (4) can be plotted as a function of two tool parameters for varying the depth at which the reflection signal (4) originates. For example the applied pump laser (3) power ($P_{gen}$) and the offset (d) between both laser beams (3,6) can be varied. By varying the power of the pump laser (3) a power curves is obtained while by varying, for each of the m values of the pump laser power, the offset (d) a set of at least two offset curves is obtained. Hence by varying these two tool parameters independently both the active carrier profile and the second parameter profile can be scanned simultaneously over a predetermined depth range. As a result a set of 2 measurement values {Q,I} is obtained for every combination of these parameters $P_{gen}$ and d. The current extraction method thus comprises the generation of 4 m measurement values for m measurement points P (power curve) and m measurement points J (offset curve).

At each of the 2 m measurement points d and P, i.e. at each depth measured, the four independent values $Q(P)_j$, $I(P)_j$, $Q(d)_j$, $I(d)_j$ obtained during these measurements are correlated with the four unknown parameters, being the active carrier profile $Z_j$ (depth at position j) and $C_j$ (=carrier concentration at position j) and the second parameter (e.g. defect density/recombination rate) profile $W_j$ (depth at position j) and $D_j$ (=second parameter concentration at position j) corresponding to that measurement depth. The current extraction method thus comprises correlating the set of 4 m independent measurement values $\{Q(P)_j, I(P)_j, Q(d)_j, I(d)_j\}$ with j: 0→m, with the set of 4 m independent carrier profile values $\{C_j, Z_j, D_j, W_j\}$ with j: 0→m.

The 4 m unknown values $\{C_j, Z_j, D_j, W_j\}$ with j: 0→m can be extracted uniquely from the 4 m measured values $\{Q(P)_j, I(P)_j, Q(d)_j, I(d)_j\}$ with j: 0→m, by following the following iterative solution scheme:

(i) Measure the 4 m experimental reflected signals $I(P)_j+iQ(P)_j$ and $I(d)_j+iQ(d)_j$, j: 0→m on the unknown structure with a general profile by varying two independent selected tool parameters, e.g. for example pump laser power (P) and beam offset (d).

(ii) Choose carrier concentration and corresponding junction depth and also second parameter concentration and corresponding junction depth starting values $(C_j^o, Z_j^o, D_j^o, W_j^o)$ for each of the 4 m unknown variables $(C_j, Z_j, D_j, W_j)$.

(iii) Use a device simulator to calculate the photo-induced in depth varying excess carrier (N(z)) and temperature profile (T(z)) within the doped structure based on the solution of among others the Poisson equation, the current equations and temperature diffusion equations and appropriate physical models involving among others the necessary generation, absorption and recombination models.

(iv) Determine the (complex) refractive index profile (n(z)=F(N(z),T(z)) with F a non-linear function) due to the presence of the above-calculated excess carrier (N(z)) and temperature (T(z)) depth profiles, among others based on the application of the Drude model.

(v) Calculate the 4 m corresponding (expected) TP signals $I(P)_j^o+iQ(P)_j^o$ and $I(d)_j^o+iQ(d)_j^o$ from multi-layer reflection theory based on the shape of n(z) and the value of the two selected tool parameters (pump laser power, beam offset, time) for j: 0→m.

(vi) Compare the initially 4 m simulated signals $I(P)_j^o+iQ(P)_j^o$ and $I(d)_j^o+iQ(d)_j$ with the 4 m experimentally recorded $I(P)_j+iQ(P)_j$ and $I(d)_j+iQ(d)_j$ signals, determine the error (difference) between both in 4 m-dimensional space by an appropriate mathematical measure and adapt the 4 m independent variables $C_j^o, Z_j^o, D_j^o, W_j^o$ for j: 0→m in order to improve the initial guess for the unknown carrier concentration $C_j$ and its junction depth $Z_j$, and the unknown second parameter concentration $D_j$ and its junction depth $W_j$ values. The latter can be done by specialized mathematical non-linear problem solvers which are commercially available.

(vii) Go to step (iii) above and continue this iterative non-linear process until the unique solution $(C_j, Z_j, D_j, W_j)$ which defines the complete unknown carrier depth profile and unknown second parameter (e.g. defect density/recombination rate) depth profile has been found. The series of intermediate solutions $(C_j^i, Z_j^i, D_j^i, W_j^i)$ (until convergence has been reached) can be represented by a non-linear curve in a 4 m-dimensional plane. Given the fact that there are only 4 m unknown parameters for two general profiles to be determined in m different depth locations, m different TP measurements as a function of two independent tool parameters with each two independent signals suffice to extract the required characteristics (carrier and second parameter concentration and both of their junction positions for each of the m different depths).

As illustrated by FIG. 12 one can choose as the two independent tool parameters, the pump power for generating power curves and the beam offset for generating offset curves. The density of the excess carriers will vary in the depth z into the substrate (1). Due to the dependence of the lateral diffusion of the excess carriers on their density, i.e. lower lateral diffusion for higher density, the offset curves are able to scan the whole depth profile through modification of the offset (d) between the pump laser beam (6) and the probe laser beam (3). The presence of a localized defect density depth profile, for example generated when annealing an implanted dopant profile only for very short time anneals mainly affects the Schockley-Read-Hall (SRH) recombination rates. Hence changing the pump power will allow for scanning excess carrier level from a low value, where SRH recombination dominates to a high value, where Auger recombination dominates. By simultaneously probing the substrate (1) at different junction depths by varying the offset (d), the simultaneous deconvolution of the underlying defect related information D(z) and the excess carrier profile C(z) can be obtained.

Figure 13A:
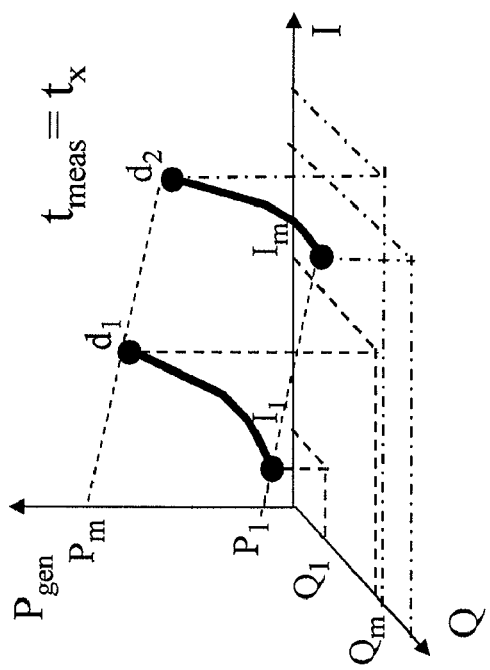
FIG. 13 illustrates the correlation between (a) measurement curve whereby pump laser power is varied with two values for the offset and (b) active dopant profile (left), second parameter profile (right) of the semiconductor substrate under study according to an embodiment of the present invention.
Figure 13B:
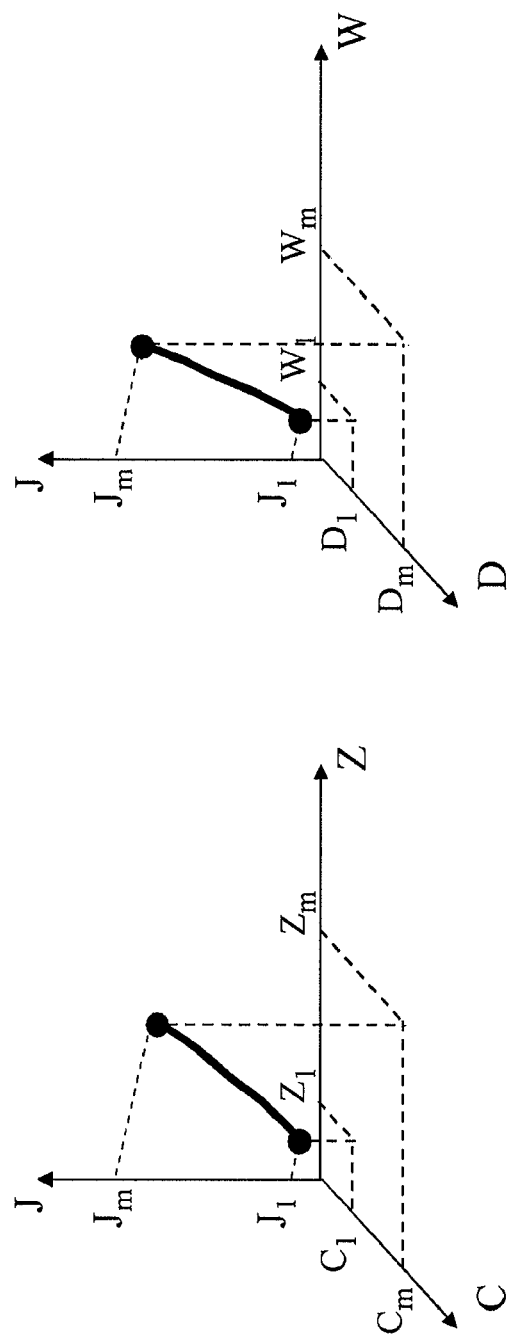

In a first embodiment of this aspect of the invention the power of the pump laser (6) and the offset between the probe laser (3) and the pump laser (6) is varied, while the time during which each of the 4 m measurements is performed is kept constant. State-of-the art TP systems are modified to allow the increase and decrease of the pump laser power and to vary the offset. By enabling the variation of the pump laser in both directions a large enough dynamic range can be obtained as illustrated by FIG. 7. Here for each setting of the tool parameter $P_{gen}$ corresponding excess carrier profiles (7) are generated which intersects with the doping profile (5). Also shown in FIG. 7 are the reflection of the probe signal at this intersection $E_{interface}$ and the reflection at or near the surface $E_{surface}$. This tool parameter variation will result in a three-dimensional measurement curve at a first value $d_1$ of the offset d, which can be represented by: $Q(P_{gen,j}, d_1)$, $I(P_{gen,j} d_1)$ where $P_{gen}$ is the pump laser power as illustrated by FIG. 13a. By varying the offset (d) another three-dimensional measurement curve can be obtained which can be represented by $Q(P_{gen,j}, d_2)$, $I(P_{gen,j} d_2)$ as shown in FIG. 13a. Using the extraction procedure illustrated by the flowchart of FIG. 12 simultaneously the active carrier profile (C,Z) and second parameter profile (D, W) can be determined as illustrated by FIG. 13b, respectively left and right.

Figures 14A, 14B:
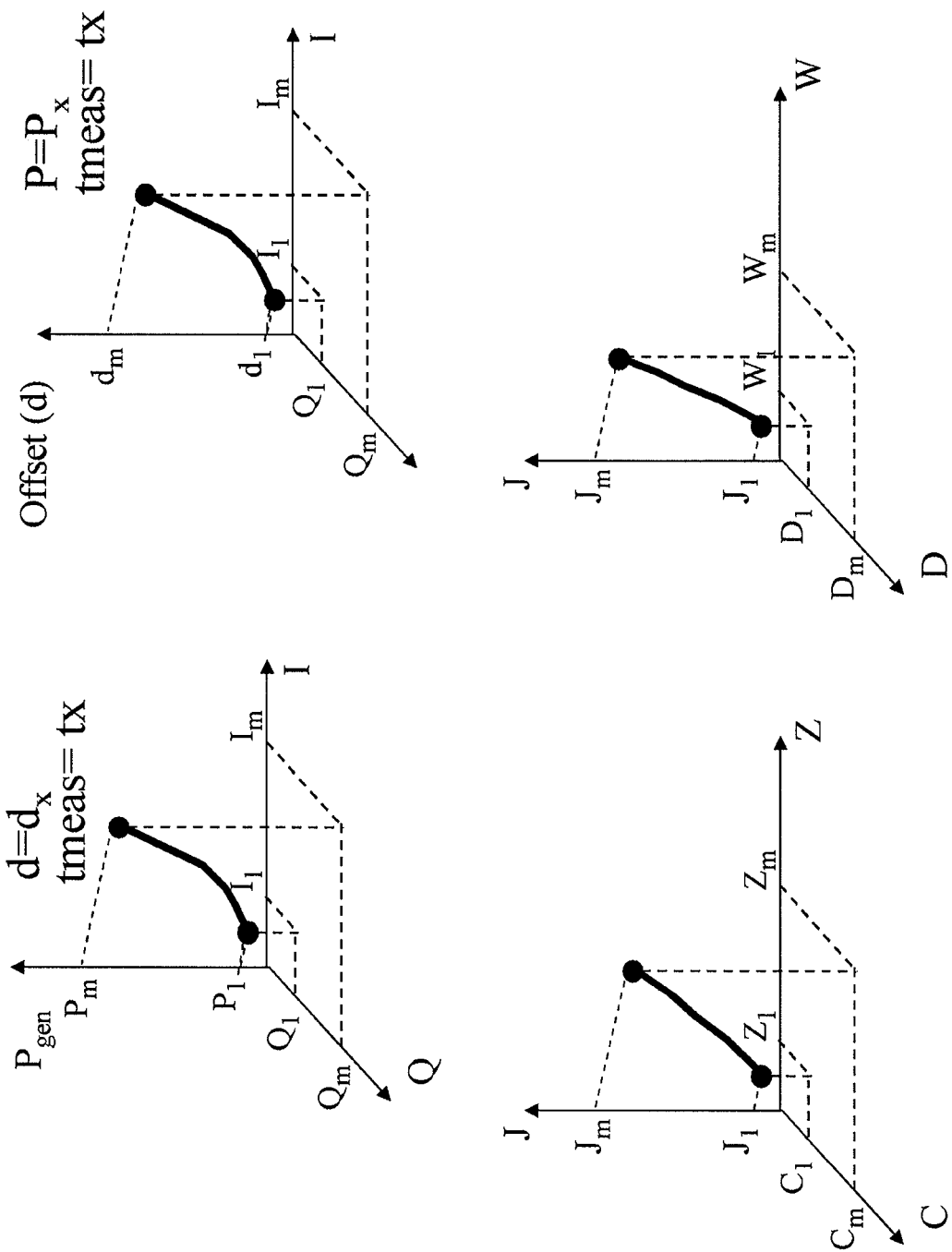
FIG. 14 illustrates the correlation between (a) measurement curves whereby pump laser power is varied for given offset (left: power curve) and the offset is varied for given pump laser power (right: offset curve) and (b) active dopant profile (left), second parameter profile (right) of the semiconductor substrate under study according to an embodiment of the present invention.

As illustrated by FIG. 14a-b one can obtain the 2 m measurement points by first measuring a power profile curve (FIG. 14a left) with constant offset $d=d_x$. thereby obtained m measurement points $Q(P_{gen,j}, d_x)$, $I(P_{gen,j} d_x)$. Then an offset profile curve is measured (FIG. 14a right) with constant pump laser power $P=P_x$. The level of the pump laser power can be selected to generate a high number of excess carriers in the substrate in which case only auger recombination is to be taken into account. For lower levels of the pump laser power a low number of excess carriers is generated in the substrate in which case the Schockly-Read-Hall recombination mechanism will dominate the recombination process. Using the extraction procedure illustrated by the flowchart of FIG. 12 simultaneously the active carrier profile (C,Z) and second parameter profile (D, W) can be determined as illustrated by FIG. 14b, respectively left and right.

In a second embodiment of this aspect of the invention the period $t_{meas}$ during which the reflected probe signal (4) is observed and the power of the probe signal (3) is varied while the offset between the probe laser (3) and the pump laser (6) is kept constant. The measured signals Q, I are time dependent, i.e. a strong non-linear increase is observed between the measured signals Q, I as function of the measurement time $t_{mea}$, probably due to injection of carriers from the semiconductor substrate into a dielectric layer, e.g. a silicon oxide layer, covering the surface of this semiconductor substrate (1). Typically a saturation level of the measured signals Q, I is reached after about 1000 seconds, while the recovering time may be weeks. Plotting the independent signals Q, I versus time gives a measurement curve in a three-dimensional space Q, I and $t_{meas}$ is obtained. For example one can perform at each of the m values of the pump laser power at least two reflectance measurements for different measurement period $t_{meas}$.

In a third embodiment of this aspect of the invention the period $t_{meas}$ during which the reflected probe signal (4) is observed and the offset between the probe laser (3) and the pump laser (6) is varied while the power of the probe signal (3) is kept constant. The measured signals Q, I are time dependent, i.e. a strong non-linear increase is observed between the measured signals Q, I as function of the measurement time $t_{mea}$, probably due to injection of carriers from the semiconductor substrate into a dielectric layer, e.g. a silicon oxide layer, covering the surface of this semiconductor substrate (1). Typically a saturation level of the measured signals Q, I is reached after about 1000 seconds, while the recovering time may be weeks. Plotting the independent signals Q, I versus time gives a measurement curve in a three-dimensional space Q, I and $t_{meas}$ is obtained. For example one can perform at each of the m values of the offset (d) at least two reflectance measurements for different measurement period $t_{meas}$.

In a fourth aspect of the invention, up to [n.k] (which represents the result of multiplying n by k and may equally be noted as n*k) independent profiles for multiple material parameters, i.e. the active dopant profile, the temperature, the defect density, the recombination speed for electrons, the recombination speed for holes, . . . are simultaneously extracted. Each parameter profile will have up to m profile points. The methods disclosed in the previous aspects of the invention can be applied to generate a sufficient number of measurement points and to correlate these measurement points with the profiles to be extracted. One can generate [n.k] measurement curves, whereby each measurement curves comprises m measurement points, each measurement point comprising 2 independent measurement signals, e.g. (Q, I) components of a TP signal. These [n.k].m measurement points are correlated with up to [n.k].m profile points of the [n.k] material parameter profiles, each of the m profile points comprising a concentration value C with its corresponding depth value Z. Hence this allows correlating [n.k] [m.2] (which represents the result of multiplying n by k and by m and by 2 and may equally be noted as n*k*m*2) independent measurement values obtained using a non-destructive optical measurement technique with [n.k] [m.2] independent parameter profile values. The numbers m, n, k correspond to the values set for the depth varying means, being respectively the power of the pump laser beam, the offset between the pump laser beam and the probe laser beam and the measurement timed during which the reflected probe signal is measured. The numbers m, n, k are integers.

For any shape of the parameter profiles, for example Gaussian shaped profiles, the variation in the power parameters amplitude (A) and phase angle (phi) of the probe laser signal reflected by the sample (4) can be plotted as a function of the tool parameters for varying the depth at which the reflection signal (4) originates. For example the applied pump laser (3)

power (Pgen) [m], the offset (d) between both laser beams (3,6) [n] and the time during $t_{meas}$ during which the reflected signal is measured [k] can be varied. By varying the power (P) of the pump laser (3) a power curve with m measurement points is obtained, by varying for each of the m values of the pump laser power the offset (d) a set of n offset curves is obtained and by varying the measurement time $t_{meas}$ a set of k time curves is obtained. Hence by varying these three tool parameters independently up to [n.k] material parameter profiles can be scanned simultaneously over a predetermined depth range. As a result a set of 2 [m.n.k] measurement values {Q,I} is obtained for every combination of these parameters $P_{gen}$, d and $t_{meas}$. The current extraction method thus comprises the generation of up to 2 [m.n.k] measurement values for m measurement points P (power curve), n measurement points J (offset curve) and k measurement points L (time curve).

At each of the [m.n.k] measurement points P, d and $t_{meas}$, i.e. at each depth measured, the independent values $Q(P, d, t_{meas})_{jr}$, $I(P, d, t_{meas})_{jr}$ obtained during these measurements are correlated with the [n.k].m unknown parameter profile points, each parameter having a level value $C_j$ (level at position j) and a depth value $Z_j$. The current extraction method thus comprises correlating the set of [n.k].m.2 independent measurement values $\{Q(P, d, t_{meas})_{jr}, I(P, d, t_{meas})_{jr}\}$ with j: 0→m, and r: 0→n.k with the set of [n.k].m.2 independent carrier profile values $\{C_j, Z_j\}_r$ with j: 0→m and r: 0→n.k.

Figure 15:
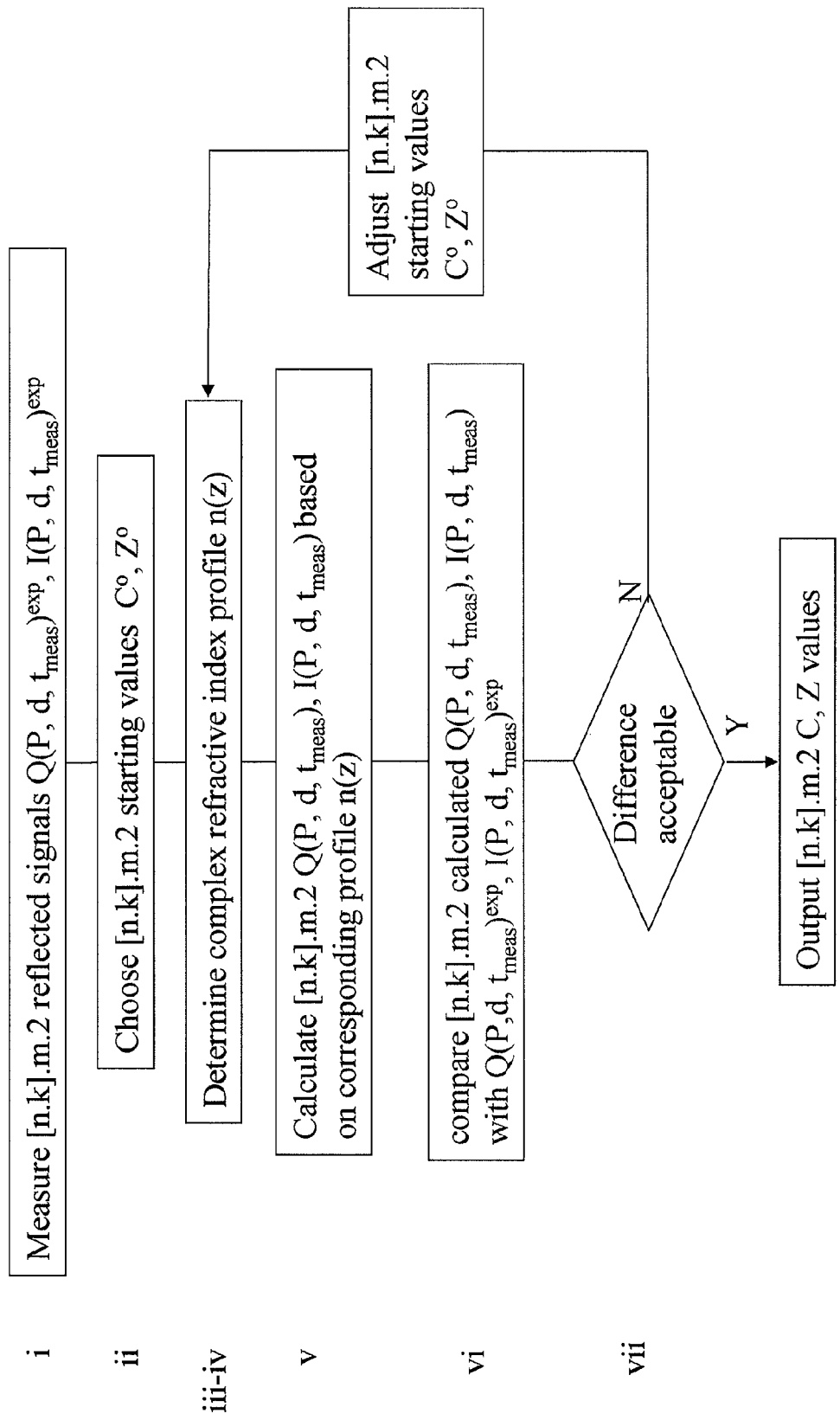
FIG. 15 is a flow chart illustrating an extraction method for a complete [n.k] parameter profiles (C, Z) according to an embodiment of the present invention.

The [n.k].m.2 unknown values $\{C_j, Z_j\}_r$ with j: 0→m and r: 0→n.k can be extracted uniquely from the [n.k].m.2 measured values $\{Q(P, d, t_{meas})_{jr}, I(P, d, t_{meas})_{jr}\}$ with j: 0→m, and r: 0→n.k by following the following iterative solution scheme, as illustrated by FIG. 15:

(i) Measure the [n.k].m.2 experimental reflected signals $Q(P, d, t_{meas})_{jr}$, $I(P, d, t_{meas})i_{jr}$ j: 0→m and r: 0→n.k on the unknown structure with a general profile by varying three independent selected tool parameters, e.g. pump laser power (P), beam offset (d) and measurement time $(t_{meas})$ (ii) Choose for each of the [n.k] parameters a level value C and corresponding junction depth Z starting values $\{(C_j^o, Z_j^o)_r\}$ for each of the [n.k].m.2 parameter values variables $\{(C_j, Z_j)_r\}$.

(iii) Use a device simulator to calculate the photo-induced in depth varying excess carrier (N(z)) and temperature profile (T(z)) within the doped structure based on the solution of among others the Poisson equation, the current equations and temperature diffusion equations and appropriate physical models involving among others the necessary generation, absorption and recombination models.

(iv) Determine the (complex) refractive index profile (n(z)=F(N(z),T(z)) with F a non-linear function) due to the presence of the above-calculated excess carrier (N(z)) and temperature (T(z)) depth profiles, among others based on the application of the Drude model.

(v) Calculate the [n.k].m.2 corresponding (expected) TP signals $Q(P, d, t_{meas})_{jr}$, $I(P, d, t_{meas})_{jr}$ from multi-layer reflection theory based on the shape of n(z) and the value of the three selected tool parameters (pump laser power, beam offset, time) for j: 0→m and r: o→n.k.

(vi) Compare the initially [n.k].m.2 simulated signals $Q(P, d, t_{meas})_{jr}$, $I(P, d, t_{meas})_{jr}$ with the [n.k].m.2 experimentally recorded $Q(P, d, t_{meas})_{jr}$, $I(P, d, t_{meas})_{jr}$ signals, determine the error (difference) between both in [n.k].m.2-dimensional space by an appropriate mathematical measure and adapt the [n.k].m.2 independent variables $(\{C_j^o, Z_j^o\}_r)$ j: 0→m and r: 0→n.k in order to improve the initial guess for the unknown level value $C_j$ and its junction depth $Z_j$. The latter can be done by specialized mathematical non-linear problem solvers which are commercially available.

(vii) Go to step (iii) above and continue this iterative non-linear process until the unique solution $(C_j, Z_j)_r$ which defines the complete unknown parameter profile. The series of intermediate solutions $(C_j^i, Z_j^i)$ (until convergence has been reached) can be represented by a non-linear curve in a [n.k].m.2-dimensional plane. Given the fact that there are only [n.k].m.2 unknown parameter values for [n.k] different profiles to be determined in m different depth locations, m different TP measurements as a function of three independent tool parameters with each two independent signals suffice to extract the required characteristics (concentration level and junction depth of [n.k] different profiles for each of the m different depths).

It is to be understood that although preferred embodiments, specific constructions and configurations, as well as materials, have been discussed herein for devices according to the present invention, various changes or modifications in form and detail may be made without departing from the scope and spirit of this invention. For example, the substrate used in the description above is silicon, but may as well be any other suitable semiconductor material such as e.g. germanium (Ge), silicon-germanium (SiGe) or a combination of III-V materials such as galliumarsenide (GaAs). Instead of analyzing a bulk semiconductor wafer other substrate types such as a silicon-on-insulator (SOI) or a germanium-on-insulator (GOI) substrate can be analyzed using this technique.

Figure 16:
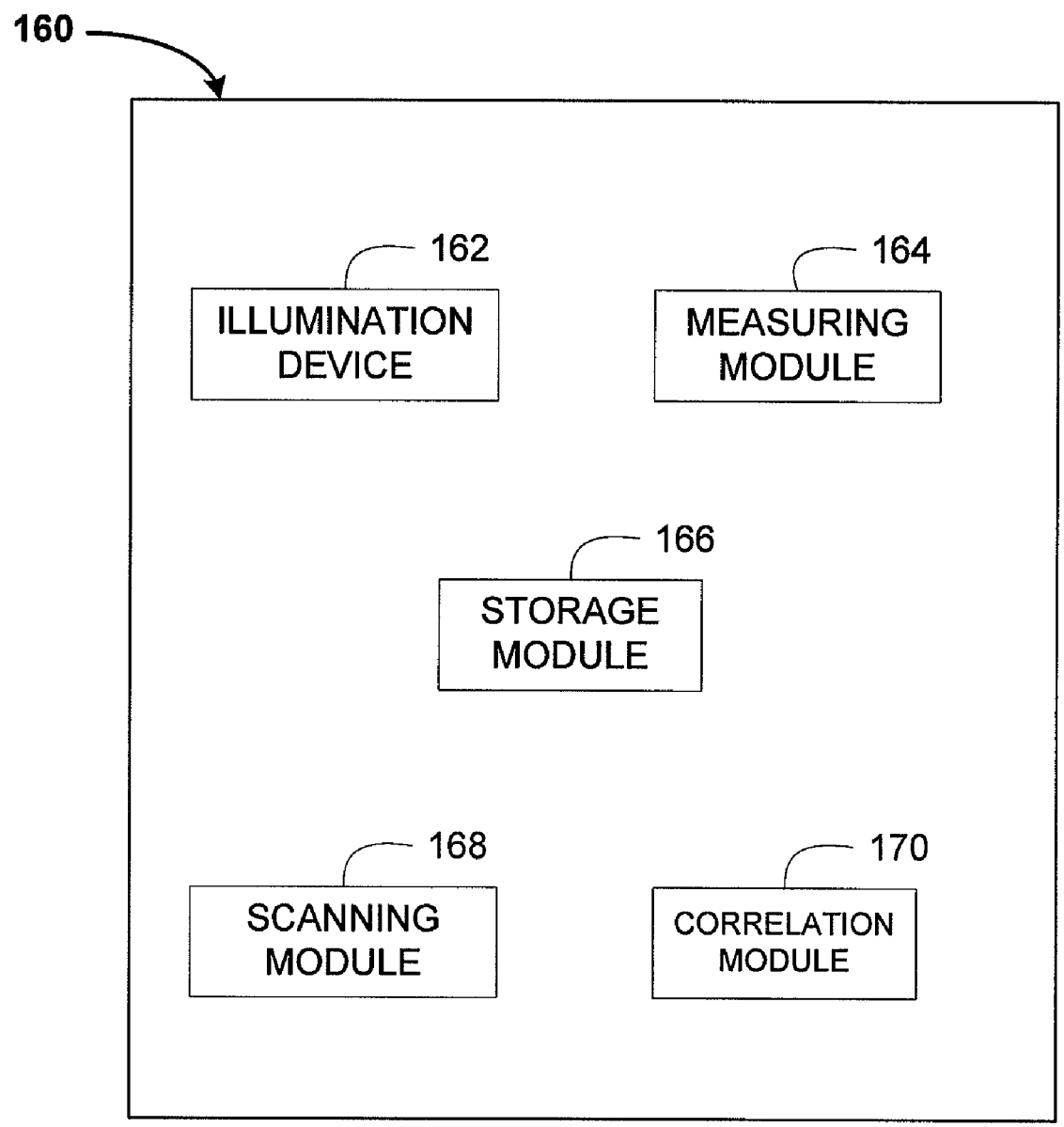
FIG. 16 shows a block diagram illustrating one embodiment of an apparatus for determining at least an active carrier profile of a semiconductor substrate.

FIG. 16 shows a block diagram illustrating one embodiment of an apparatus for determining at least an active carrier profile of a semiconductor substrate. The apparatus 160 may comprise an illumination device 162. The illumination device further comprises a pump laser unit configured to emit a pump laser 6 (as describe above in FIG. 1) thus creating excess carriers in the substrate, and a probe laser unit configured to impinge a probe laser beam 3 (as described above in FIG. 1), at least partially reflected by the excess carriers, on the semiconductor substrate, thus generating a reflection signal. The apparatus 160 may further comprise a measuring module 164 configured to measure the reflection signal. The apparatus 160 may further comprise a scanning module 168 configured to scan the active carrier profile when measuring the reflection signal. The apparatus 160 may further comprise a storage module 166 configured to store at least m measured reflection signals, each reflection signal comprising two independent signals. The apparatus 160 may further comprise a correlating module configured to correlate the at least m measured reflection signals with m profile points, each profile point comprising an active carrier concentration C and the corresponding depth Z, with m being an integer value.

Figure 17:
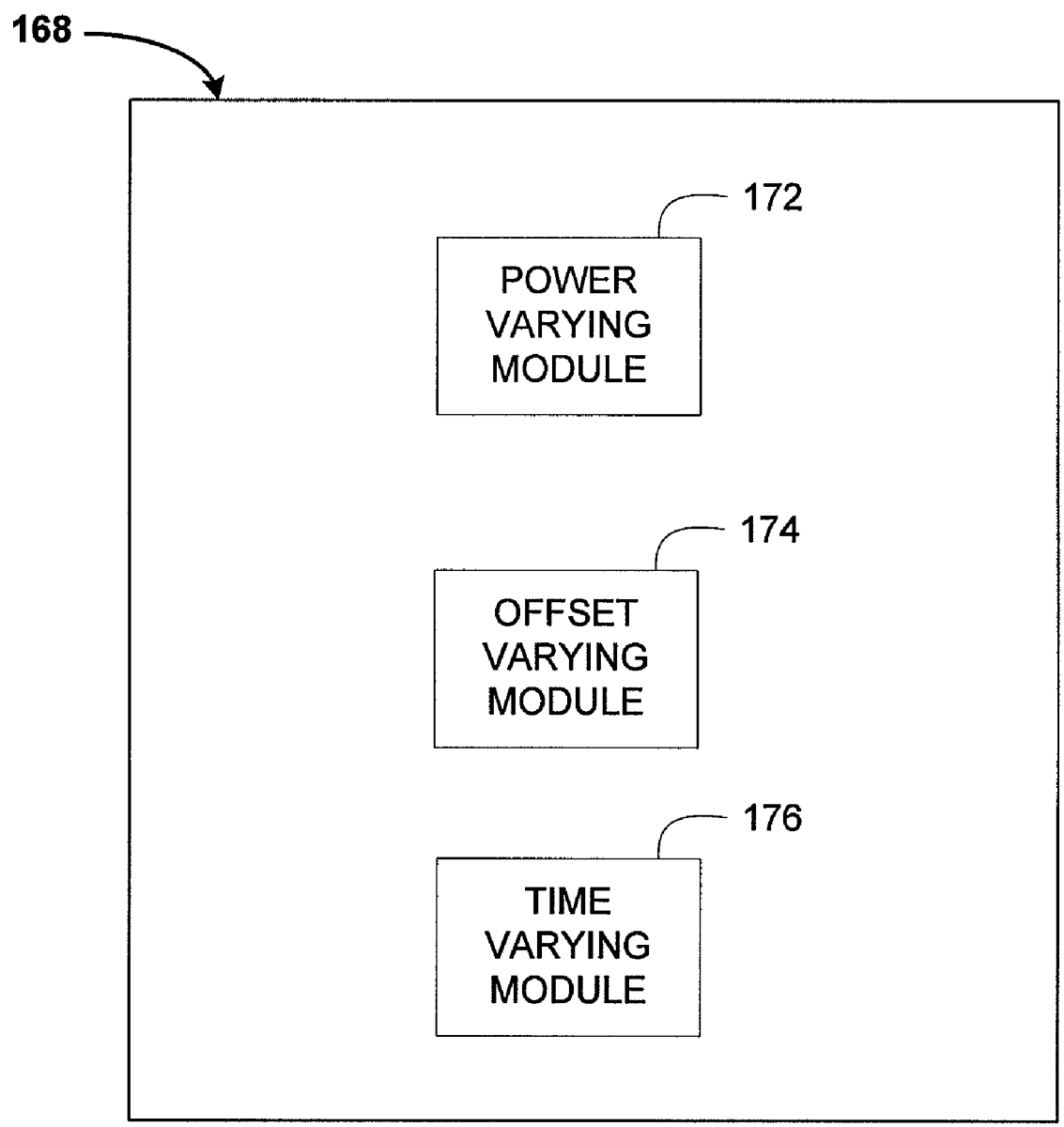
FIG. 17 shows a block diagram illustrating one embodiment of a scanning module.

FIG. 17 shows a block diagram illustrating one embodiment of a scanning module 168 in FIG. 16. Depending on the embodiment, certain functional modules may be removed, merged together, or rearranged in order.

The scanning module 168 may comprise a power varying module 172 configured to vary the power of the probe laser produced by the probe laser unit of the illumination device 162 (see FIG. 16). The scanning module 168 may further comprise an offset varying module 174 configured to vary the offset d between the pump laser and the probe laser. The scanning module 168 may further comprise a time varying module 176 configured to vary the time during which each reflection signal is measured.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A method of using optical measurement to determine at least an active carrier profile of a semiconductor substrate, the profile being expressed as a set of concentration values C with corresponding depths Z, the method comprising:
   generating m measurement points, each measurement point comprising two independent measurement signals; and
   correlating these m measurement points with m active carrier profile points, each active carrier profile point comprising an active carrier concentration C and the corresponding depth Z, with m being an integer value.

2. The method of claim 1, wherein generating m measurement points comprises:
   providing a pump laser;
   providing a probe laser;
   focusing the pump laser and the probe laser on the semiconductor substrate, the pump laser generating in an area of the semiconductor substrate contacted by the pump laser a number of excess charge carriers, having a depth profile, the generated excess charge carriers reflecting the beam of the probe laser; and
   detecting two independent predetermined characteristics of the reflected probe laser beam.

3. The method of claim 2, wherein
   the pump laser is selected to create excess carrier plasma waves, and
   the two independent signals are the amplitude and the phase of the reflected probe laser.

4. The method of claim 2, wherein generating m measurement points comprises:
   either applying m different values of the power of the probe laser; or
   applying m different offsets between the pump laser and the probe laser; or
   detecting two independent predetermined characteristics of the reflected probe laser beam during m different time periods.

5. The method of claim 1, wherein correlating the m measurement points with the m profile points comprises:
   selecting values for the active concentration and corresponding depth for each of the m profile points;
   simulating the excess carrier concentration using these selected values to determine the complex refraction index profile of the substrate;
   determining m values for each of the two independent measurement signals using the simulated refraction index profile;
   determining the difference between the m determined values with the m measured values for each of the two independent measurement signal; and
   repeating the above steps until an unique solution for the active carrier profile is obtained.

6. The method of claim 2, further comprising determining at least another material parameter profile of the semiconductor substrate, the method comprising:
   generating m additional measurement points, each additional measurement point comprising two independent measurement signals; and
   simultaneously correlating these 2 m measurement points with m active carrier profile points, each active carrier profile point comprising an active carrier concentration C and the corresponding depth Z, and with m material parameter profile points, each material parameter profile point comprising an concentration D and the corresponding depth W with m being an integer value.

7. The method of claim 5, wherein generating m additional measurement point comprises:
   applying m different values of the power of the probe laser and for each of the m power values varying the offset (d) between the pump laser and the probe laser.

8. The method of claim 5, wherein generating m additional measurement point comprises:
   applying m different values of the power of the probe laser and for each of the m power values varying the time period $t_{meas}$ for detecting the two independent predetermined characteristics of the reflected probe laser beam; or
   applying m different values of the offset (d) between the pump laser and the probe laser and for each of the m offset values varying the time period $t_{meas}$ for detecting the two independent predetermined characteristics of the reflected probe laser beam.

9. The method of claim 5, wherein correlating the 2 m measurement points with the 2 m profile points comprises:
   selecting values for the active concentration and corresponding depth for each of the m active carrier profile points;
   selecting values for the material parameter concentration and corresponding depth for each of the m material parameter profile points;
   simulating the excess carrier concentration using these selected values to determine the complex refraction index profile of the substrate;
   determining 2 m values for each of the two independent measurement signals using the simulated refraction index profile;
   determining the difference between the 2 m determined values with the 2 m measured values for each of the two independent measurement signals; and
   repeating the above steps until an unique solution for the active carrier profile and for the second parameter profile is obtained.

10. The method of claim 1, further comprising determining multiple material parameter profiles of the semiconductor substrate, the method comprising:
    generating ([n.k]−1).m additional measurement points, each additional measurement point comprising two independent measurement signals; and
    simultaneously correlating these [n.k].m measurement points with m active carrier profile points, each active carrier profile point comprising an active carrier concentration C and the corresponding depth Z, and with ([n.k]−1).m material parameter profile points, each material parameter profile point comprising an concentration D and the corresponding depth W with n, k, m being integer values.

11. The method of claim 10, wherein generating [n.k].m measurement points comprises:
applying m different values of the power of the probe laser;
for each of the m power values, applying n different values of the offset (d) between the pump laser and the probe laser; and
for each of the n offset values, applying k different values for the time period $t_{meas}$ for detecting the two independent predetermined characteristics of the reflected probe laser beam.

12. The method of claim 10, wherein correlating the [n.k].m measurement points with the [n.k].m profile points comprises:
selecting values for the active concentration and corresponding depth for each of the m active carrier profile points;
selecting values for the material parameter concentration and corresponding depth for each of the ([n.k]−1) m material parameter profile points;
simulating the excess carrier concentration using these selected values to determine the complex refraction index profile of the substrate;
determining [n.k].m values for each of the two independent measurement signals using the simulated refraction index profile;
determining the difference between the [n.k].m determined values with the [n.k].m measured values for each of the two independent measurement signals; and
repeating the above steps until an unique solution for the active carrier profile and for the second parameter profile is obtained.

13. A computer program product for executing the method of claim 1 when being executed on a computer device.

14. A machine-readable medium storing a computer program configured to perform the method of claim 1.

15. An apparatus for determining at least an active carrier profile of a semiconductor substrate comprising:
an illumination device comprising:
a pump laser configured to create excess carriers in the substrate; and
a probe laser configured to impinge a laser beam, at least partially reflected by the excess carriers, on the semiconductor substrate, thus generating a reflection signal;
a measuring module configured to measure the reflection signal;
a scanning module configured to scan the active carrier profile when measuring the reflection signal;
a storage module configured to store at least m measured reflection signals, each reflection signal comprising two independent signals; and
a correlating module configured to correlate the at least m measured reflection signals with m profile points, each profile point comprising an active carrier concentration C and the corresponding depth Z, with m being an integer value.

16. The apparatus of claim 15, wherein the scanning module further comprises a power varying module configured to vary the power of probe laser.

17. The apparatus of claim 15, wherein the scanning module further comprises an offset varying module configured to vary the offset d between the pump laser and the probe laser.

18. The apparatus of claim 15, wherein the scanning module comprises a time varying module configured to vary the time during which each reflection signal is measured.

19. The apparatus of claim 15, wherein the storage module is adapted for storing 2 m measured reflection signals and the correlating module is adapted for correlating 2 m measured reflection signals with m active carrier profile points and with m second parameter profile points, each profile point comprising a concentration and the corresponding depth, with m being an integer value.

20. The apparatus of claim 19, wherein the scanning module comprises two or more of the following:
a power varying module configured to vary the power of probe laser;
an offset varying module configured to vary the offset d between the pump laser for creating excess carriers and the probe laser; and
a time varying module configured to vary the time during which each reflection signal is measured.

21. The apparatus of claim 15, wherein
the storage module is adapted for storing [n.k].m measured reflection signals; and
the correlation module is adapted for correlating [n.k].m measured reflection signals with m active carrier profile points and with ([n.k]−1)m material parameter profile points, each profile point comprising a concentration and the corresponding depth, with m, n, k being integer values.

22. The apparatus of claim 21, wherein the scanning module comprises:
a power varying module configured to vary the power of probe laser;
an offset varying module configured to vary the offset d between the pump laser and the probe laser; and
a time varying module configured to vary the time during which each reflection signal is measured.

23. A system for using optical measurement to determine at least an active carrier profile of a semiconductor substrate, the profile being expressed as a set of concentration values C with corresponding depths Z, the system comprising:
means for generating m measurement points, each measurement point comprising two independent measurement signals; and
means for correlating these m measurement points with m active carrier profile points, each active carrier profile point comprising an active carrier concentration C and the corresponding depth Z, with m being an integer value.

24. An apparatus for determining at least an active carrier profile of a semiconductor substrate comprising:
an illumination device comprising:
means for creating excess carriers; and
means for impinging a probe laser beam, at least partially reflected by the excess carriers, on the semiconductor substrate, thus generating a reflection signal;
means for measuring the reflection signal;
means for scanning the active carrier profile when measuring the reflection signal,
means for storing at least m measured reflection signals, each reflection signal comprising two independent signals; and
means for correlating the at least m measured reflection signals with m profile points, each profile point comprising an active carrier concentration C and the corresponding depth Z, with m being an integer value.

* * * * *